United States Patent [19]

Betts et al.

[11] Patent Number: 5,338,435
[45] Date of Patent: Aug. 16, 1994

[54] INTEGRATED CIRCUIT HYDRATED SENSOR APPARATUS

[75] Inventors: Ronald E. Betts, La Jolla; Douglas R. Savage, Del Mar; Richard J. Koerner, San Diego; Matthew J. Leader, Laguna Niguel, all of Calif.; Kee V. Sin, Lino Lakes, Minn.; Jeffrey A. Graves, San Juan Capistrano; Marshall L. Sherman, Cardiff, both of Calif.

[73] Assignee: PPG Industries, Inc., Pittsburgh, Pa.

[21] Appl. No.: 905,255

[22] Filed: Jun. 26, 1992
(Under 37 CFR 1.47)

Related U.S. Application Data

[63] Continuation-in-part of Ser. No. 721,025, Jun. 26, 1991, abandoned, and a continuation-in-part of Ser. No. 721,030, Jun. 26, 1991, abandoned.

[51] Int. Cl.$^5$ .................................................. G01N 27/26
[52] U.S. Cl. ........................................ 204/406; 204/408; 204/409; 204/412; 204/416; 204/415; 204/153.17; 128/635
[58] Field of Search .............. 204/406, 408, 409, 412, 204/416, 422, 433, 435, 400, 415, 153.1, 153.17; 338/22 R; 128/635; 219/209, 121.6

[56] References Cited

U.S. PATENT DOCUMENTS

| | | | |
|---|---|---|---|
| 3,000,805 | 9/1961 | Carritt | 204/195 |
| 3,049,118 | 8/1962 | Arthur et al. | 128/2 |
| 3,088,905 | 5/1963 | Glover | 204/195 |
| 3,395,265 | 7/1968 | Weir | 219/209 |
| 3,440,397 | 4/1969 | Vesper et al. | 219/209 |
| 3,440,407 | 4/1969 | Goltsos et al. | 219/494 |
| 3,497,442 | 2/1970 | Vincent | 204/195 |
| 3,887,785 | 6/1975 | Ahlport | 219/209 |
| 3,912,614 | 10/1975 | Spracklen et al. | 204/195 B |
| 4,041,440 | 8/1977 | Davis et al. | 338/195 |
| 4,133,735 | 1/1979 | Afromowitz et al. | 204/195 G |
| 4,284,872 | 8/1981 | Graeme | 219/121 LJ |

(List continued on next page.)

FOREIGN PATENT DOCUMENTS

| | | |
|---|---|---|
| 0015075 | 9/1980 | European Pat. Off. |
| 027385 | 4/1981 | European Pat. Off. |
| 0306158 | 3/1989 | European Pat. Off. |
| 0351516 | 1/1990 | European Pat. Off. |

OTHER PUBLICATIONS

"Technical Note: Catheter-tip Electrode for Continuous Measurement of $pO_2$ and $pCO_2$", *Medical & Biological Engineering & Computing*, vol. 16, Sep. 1978, pp. 599–600.

(List continued on next page.)

*Primary Examiner*—John Niebling
*Assistant Examiner*—Bruce F. Bell
*Attorney, Agent, or Firm*—Kenneth J. Stachel

[57] ABSTRACT

A plastic covered nonconducting substrate with an electrical circuit means is secured to the extent to withstand the presence of liquids in contact with the substrate. The covered substrate can have the substrate with one or more fluid preconditionable electrical components, a housing secured to the substrate to maintain contact of the preconditioning fluid with the electrical component like a sensor, and moisture impervious seals to cover openings in the housing for the disposition of the preconditioning fluid in the housing for contact with the electrical component on the substrate. The housing can have one or more parts and have one or more channels for containing the preconditioning fluid.

The electrical component can be an improved electronic wiring board having a thermistor and at least one blood gas sensor supported, in close relation, one to the other, on one side of the board and a heater supported on the other side of the board to provide heat in response to temperature sensed by the thermistor, to at least the region where the thermistor and the blood gas sensor are positioned on the board to control the temperature of the region of the board within a narrow distribution of temperatures.

51 Claims, 7 Drawing Sheets

U.S. PATENT DOCUMENTS

| | | | |
|---|---|---|---|
| 4,312,332 | 1/1982 | Zick | 128/635 |
| 4,356,379 | 10/1982 | Graeme | 219/209 |
| 4,450,842 | 5/1984 | Zick et al. | 128/635 |
| 4,454,007 | 6/1984 | Pace | 204/403 |
| 4,481,403 | 11/1984 | Del Monte | 219/209 |
| 4,536,274 | 8/1985 | Papadakis et al. | 204/433 |
| 4,654,127 | 3/1987 | Baker et al. | 204/406 |
| 4,734,184 | 3/1988 | Burleigh et al. | 204/409 |
| 4,786,394 | 11/1988 | Enzer et al. | 204/401 |
| 4,818,361 | 4/1989 | Burgess et al. | 204/406 |
| 4,855,572 | 8/1989 | Wallgren et al. | 219/456 |
| 4,863,016 | 9/1989 | Fong et al. | 206/210 |
| 4,929,426 | 5/1990 | Bodai et al. | 422/63 |
| 5,017,340 | 5/1991 | Pribat et al. | 204/406 |
| 5,043,692 | 8/1991 | Sites et al. | 338/28 |
| 5,046,496 | 9/1991 | Betts et al. | 204/403 |
| 5,080,865 | 1/1992 | Leiner et al. | 422/68.1 |
| 5,096,669 | 3/1992 | Lauks et al. | 422/61 |
| 5,098,545 | 3/1992 | Patko | 204/403 |
| 5,120,421 | 6/1992 | Glass et al. | 204/406 |

OTHER PUBLICATIONS

Product Information Sheets on SANCAP material. No month or year presently available.

MOCON (Modern Controls, Inc.) Product Brochure. No month or year presently available.

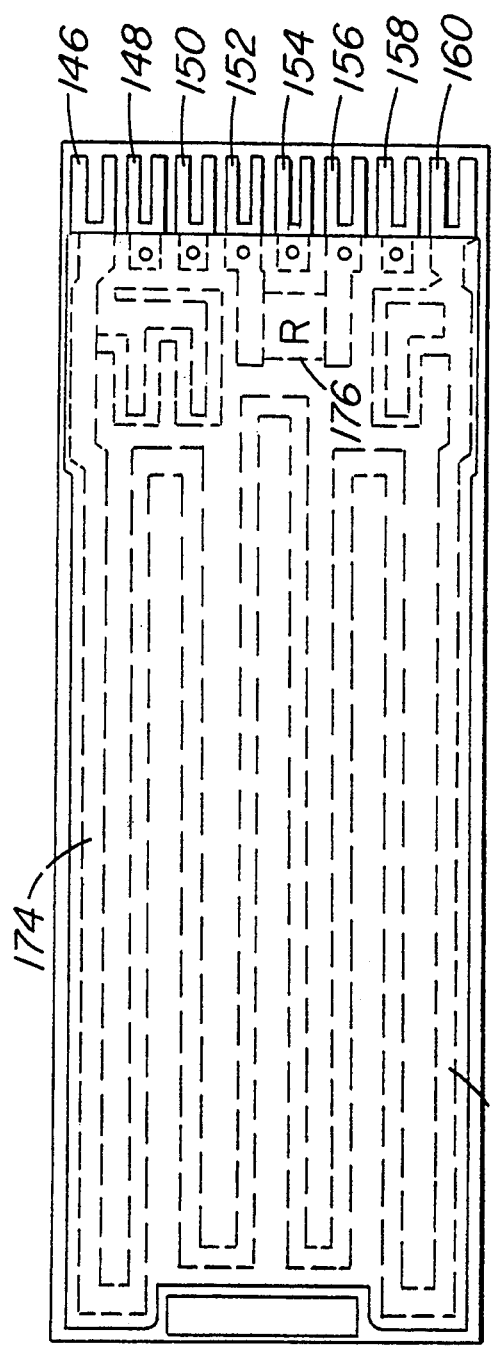
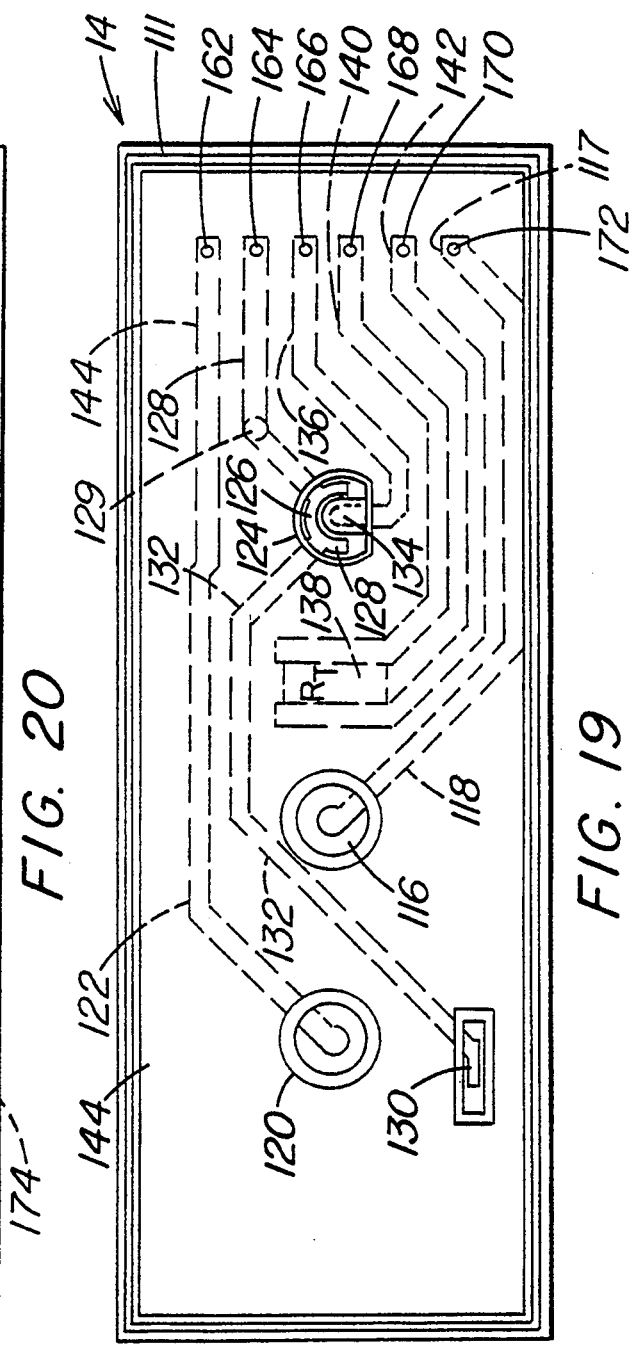

INTEGRATED CIRCUIT HYDRATED SENSOR APPARATUS

This application is a continuation in part application of Ser. Nos. 07/721,025 and 07/721,030, both filed Jun. 26, 1991, and now abandoned.

The present invention is directed to a sensor apparatus having hydrated membranes present on a nonconducting substrate that also has present an electrical circuitry. More particularly, the present invention is directed to the sensor apparatus having hydrated membranes on a ceramic substrate that has an integrated circuit produced by such techniques as silk screening, thick film and/or thin film processing.

Also the present invention is related to an improved electronic wiring substrate like a wiring board useful for detecting one or more analytes and their amounts in fluid samples.

BACKGROUND OF THE INVENTION

Numerous methods and apparatus exist in the art for measuring chemical components of fluids. For instance, when the fluid is a liquid or liquid with a dissolved gas with or without the presence of solids, it may be necessary with current technology to transport a sample to a location for testing. With centralized testing, the bulky, stationary, elaborate and sophisticated equipment performs the analysis on a practically endless number of samples. An example of this is the qualitative and/or quantitative measurement of constituents or analytes of blood. For instance, the measurement of blood gases, usually a measure of the partial pressures of oxygen and carbon dioxide, along with the pH from a sample of arterial blood gives the state of the acid base balance or the effectiveness of both the respiratory and cardiovascular systems of the human or vertebrate body. For measuring constituents of blood, the blood sample is drawn from the patient and usually, as in the case of blood gases, transported to a central location for testing.

This technique of transporting the sample to stationary measuring equipment can lead to problems. Ingenious technology has broached solutions to maintain the original composition of the fluid during transportation. Elaborate designs for syringes used in taking the blood samples overcame some problems that resulted in inaccurate readings of the particular chemical constituent being measured. For instance, for determining blood gas composition, the problem of air contamination in the collected sample was solved by the use of liquid heparin as an anticoagulant. Unfortunately, this introduced a sample dilution problem. Subsequent development resulted in the use of heparin in the dry state as opposed to the liquid state to avoid this dilution. Also, elaborate designs are provided for proper mixing of the sample after transportation but before testing. Even with these improvements, there are many reports in the literature that suggest that the values obtained in the measurement of blood gases depend on the type of measuring equipment and the technique for sample collection.

The art also has attempted to develop more portable measuring equipment rather than the fairly expensive nonportable equipment that engender the elaborate and cumbersome transportation techniques. Devices that are very portable could shorten or overcome transporting the sample altogether so that a patient's blood gases could be measured at the bedside in a manner similar to measuring a patient's temperature. U.S. Pat. Nos. 3,000,805 and 3,497,442 show two such devices. The former has electrodes located on a syringe plunger and the latter has electrodes placed on the syringe well to conduct the measurements. The electrodes are the sensing devices for the blood gases. In the allowed U.S. patent application Ser. No. 07/343,234, Applicants' assignee describes and claims a portable blood gas sensor which includes electrodes fabricated from a conventional silk screening process where the electrodes are screened on to a ceramic substance. Typically, these electrodes are used along with an electrolyte and analyte permeable membrane that covers the sensor. Some of these membranes may be hydratable membranes that can be stored in a dry state and hydrated just prior to use.

It is an object of the present invention to provide a sensor assembly apparatus that utilizes at least one hydratable membrane that can be useful in portable measuring devices or can be placed in catheter lines or actually utilized with stationary equipment where the apparatus allows for the hydrated state of the membrane. This gives the advantages of: ready-to-use sensors, establishment of a stable electronic operation with stable potential for potentiometric type sensors and maintenance of electrolytic contact between electrodes in amperometric sensors, electrolyte present for reference electrodes, and/or reduced voltage drift like that experienced during a hydration step for dry sensors with hydratable membranes.

Placement of the all of the components, including the heater, on the wiring board can result in the maximum utility and capability of these components and minimize power consumption.

SUMMARY OF THE INVENTION

The foregoing objects and others gleaned from the following disclosure are accomplished by the sensor assembly of the present invention.

The preconditioned electrochemical sensor assembly of the present invention has a sensor element that is a nonconducting substrate having at least one hydrophilic membrane and an electrical circuitry means, a housing to enclose the sensor element where the housing allows for at least one channel to pass over at least one sensor, a hydrating fluid occupying the portion or portions of the channel or channels over the sensor or sensors, and seals that are substantially impervious to at least moisture placed in or on the channel to maintain the hydrating fluid in contact with the hydrophilic membrane. The sensor and the electrical circuitry are in electrical contact with the sensor at least to convey the electrical impulses from the sensor to an instrument to read the electrical signals. Additionally, the electrical circuitry can have additional components such has additional electrodes and leads therefor and heater and temperature regulator. The housing encloses the sensor element, and the electrical circuitry of the sensor element is electrically isolated from the hydrating fluid in the channel or channels to avoid leakage current or short circuiting of the electrical circuitry means. The channel is constructed to provide fluid flow to, over, and from the one or more sensors and to allow for ingress and egress from the housing.

In a narrower aspect of the present invention, the preconditioned disposable electrochemical sensor assembly for measuring analytes in fluids has: a) a housing, b) sensor element that has a nonconducting substrate with more than one hydrophilic-membrane-containing analyte sensors and with electrical circuitry means in electrical contact with the sensors at least to convey the electrical impulses from the sensor, c) a hydrating fluid positioned in fluid contact with the hydrophilic polymeric membrane of the sensor, d) seals that are substantially impervious to at least moisture to maintain the hydrating fluid in contact with the hydrophilic polymeric membrane of the sensor, e) electrical isolating means to maintain electrical separation between the hydrating fluid and electrical circuitry means of the sensor element.

In this aspect of the invention, the housing has a first and second opposing section where each section has an exterior and interior surface. The sections when matched together form an interior space and at least one channel. The former allows for placement of the sensor element within the housing while the latter allows for fluid contact between the hydrating fluid and the hydrophilic polymeric membrane or membranes of the sensors. The channel has two opposing openings to allow fluid flow through the channel from a receiving opening before to an exit opening after the sensors. The receiving opening is suitable for attachment to a sample receiving means and the exit opening is suitable for attachment to a collection means such as a syringe or reservoir in general. The interior space of the housing communicates with the channel to contain the sensor element so that the sensor or sensors that are on the substrate are so disposed to lie in the path of the channel for fluid contact with the hydrating fluid. The first and second sections can be adhesively connected to improve their attachment to each other. The housing also allows for communication from the electrical circuitry means to the reading instrument. Such an instrument could be one that takes the signals from the sensor through the electrical circuitry and as a self-contained, hand-held, preferably battery powered monitoring instrument or analyzer processes the signals and displays the information in a digital or paper mode to the operator.

The other components of the invention are arranged in or on the housing in a manner to allow the sensor's use in detecting the component of interest in the fluid and to maintain the hydrophilic polymeric membranes of the electrochemical sensor in a hydrated state prior to use, and to isolate the hydrating fluid and the electrical circuitry means. The sensor element is configured, arranged, and placed in the interior space of the housing to assist in maintaining electrical isolation between the electrical circuitry and the hydrating fluid. The hydrating fluid is chiefly an aqueous fluid with an effective composition to hydrate at least to a partial degree but better to a substantial degree the hydrophilic polymeric membranes. The sealing means covers the receiving opening of the channel and the exit opening of the channel and can be two separate seals in adhering association to the housing so as to cover these openings. The seal can have one or more surfaces where at least one surface is substantially non-oxidizing metal such as aluminum that is useful with an adhesive-type polymer. The adhesive-type polymer can be used either as an application to the surface to be sealed or as another surface of the seal. The seal is fixedly attached to the housing by a chemical means and/or by a mechanical means. The electrical isolating means occupies an effective portion of the interior space of the housing not occupied by the sensor element or the channel and not interfering with the contact between the sensor element and the channel in order to obtain electrical isolation of the electrical circuitry means from the hydrating fluid in the channel.

The electrical circuitry means for use with the sensor element with the aforediscussed sensors and with the housing or other sensors and housings known to those skilled in the art can be an improved wiring board that includes the nonconducting substrate. In addition to the at least one analyte sensor and the substrate, the electronic wiring board of the present invention can have: 1) a thermistor in close relation to the at least one analyte sensor supported on or to the substrate, and 2) a heater, also supported on the substrate. The heater provides heat in response to the temperature sensed by the thermistor to at least the region where the thermistor and the analyte sensor are positioned on the board. This arrangement controls the temperature of the region of the board within a narrow distribution of temperatures and thereby increase the sensor's accuracy, and connecting means supported on the board for connecting the board to an external electrical source.

In a narrower aspect, the improved electronic wiring board is manufactured using thick film or thin film layered circuit technique or a combination of these, and the thermistor and the one or more analyte sensors are supported in the same plane on the substrate wherein the analyte sensors are blood gas sensors of one or more of the following types: an oxygen sensor, a carbon dioxide sensor, and a pH sensor. Also the connecting means includes plurality of external leads, and a resistor is supported on the substrate on the same side as the heater and commonly connected to one of the external leads with the thermistor, dividing the voltage therebetween. Although it is possible to have the resistor and the heater each electrically connected to external leads. The temperature coefficient of the thermistor can be positive or negative and the temperature coefficient of the resistor is substantially zero. Also the thermistor and resistor values are allowed to vary over several orders of magnitude as lone as the two can be made equal at the calibration temperature. Additionally, the connecting means further includes a plurality electronic conducting pathways individually and electrically connecting each of the sensors and the thermistor with external leads provided on the substrate at the end of the pathways.

Also, the heater can be powered by a controlled DC voltage whereby the heater is regulated by a combination of proportional, integral and/or derivative controls thereby reducing the amount of overshooting or undershooting by the heater of a predetermined temperature. The external leads are positioned on the same side of the substrate as the resistor and the heater. The electronic conducting pathways of improved electronic wiring substrate can individually and electrically connect each of the sensors and the thermistor on one side of the board with external leads provided on the other side of the board through a plurality of holes in the board. Additionally the temperature sensor including the thermistor and the resistor can be calibrated by laser trimming of the resistor to produce a ratiometric output proportional or inversely proportional to temperature.

Also, the improved electronic wiring board wherein the oxygen sensor is an electrochemical cell can have a anode and a cathode, each connected to an external lead. Also the oxygen sensor can include an oxygen permeable membrane covering, in a fluid tight manner, and an opening in the board can contain an electrolyte, and the anode can be grounded on the board to thereby assure that the potential of the electrolyte is the same as the anode potential.

Additionally, the improved electronic wiring board can have at least one reference electrode, to provide an accurate reference potential, supported on the board and it can be electrically connected to a electronic conducting pathway. Although it is possible to have one reference electrode present on the substrate and it is supported on the substrate and it is electrically connected to a electronic conducting pathway extending from the anode. The nonconducting substrate is a flat substantially thin ceramic substrate layer that has a patterned metallic layer provided on the ceramic substrate layer. The metallic layer can be formed on the substrate by depositing a metallic printing paste on the substrate to form electronic conducting pathways and the electrodes of the sensors and the electrode of a reference electrode. The metallic layer can be encapsulated with at least one layer of a chemically stable and moisture resistant encapsulant that provides electrical isolation of the electronic conducting pathways from the electrolyte and sample like blood. The wiring substrate as described can operate even after several months of storage. The thermistor provided on the ceramic substrate layer, can be encapsulated with at least one substantially thin layer of a chemically stable and moisture resistant encapsulant.

BRIEF DESCRIPTION OF THE DRAWINGS

FIG. 19 is a top planar view of one side of the wiring substrate of the present invention, having electrodes and a thermistor.

FIG. 20 is a planar view of the other side of the wiring substrate of FIG. 1 having a resistor and a heater that traverses the board and a number of leads through the substrate from the side depicted in FIG. 1 to provide an external electrical connection from the substrate.

DETAILED DESCRIPTION AND PREFERRED EMBODIMENT OF THE INVENTION

Figure 1:
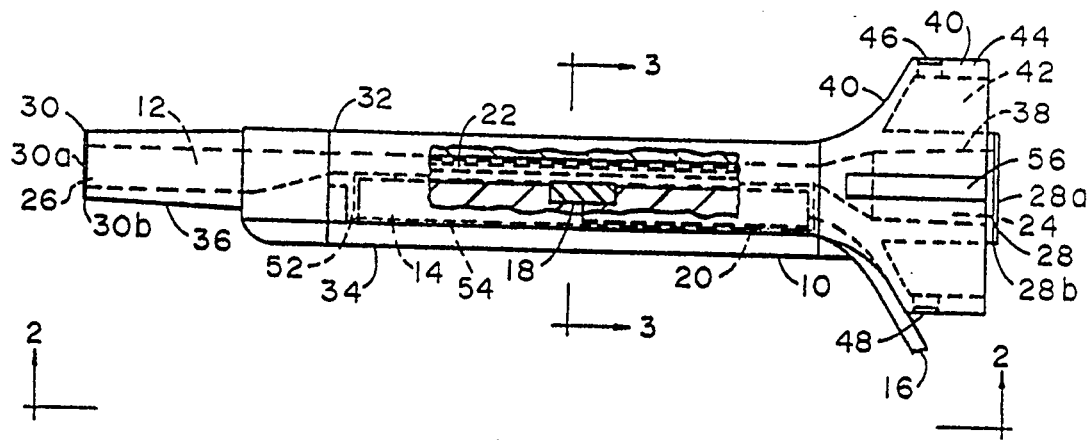
FIG. 1 is a side elevational view of the general arrangement of the sensor assembly.

In the side elevational view of FIG. 1, the general arrangement of the sensor assembly is shown. Housing 10 is made of any fairly rigid moldable material such as rigid thermoplastic polymers although thermosetting polymers can also be used. A suitable example is a methyl methacrylate styrene butadiene terpolymer and rigid plastics such as polyesters like polyethyleneterephthlate or polycarbonate or blends or alloys thereof and other similar materials known to those skilled in the art. The housing 10 can be any basic geometric shape suitable for containing a channel 12 and sensor element 14. The number of parts comprising the housing can range from 1 to a plurality, but two parts are preferred. A single part housing is at least that which sufficiently provides the channel for fluid communication with the one or more sensors 18 on sensor element 14. In this arrangement the sensor element 14 can actually form one side of the housing. The housing also supplies an opening for an electrical attachment means 16 for electric attachment to the electrical circuitry of sensor element 14. The sensor element 14 has at least one sensor 18 with a hydrophilic membrane where part of the sensor is electrically connected to electrical circuitry 20 and both the sensor 18 and electric circuit means 20 are on a nonconducting substrate of sensor element 14. The sensor 18 is located on element 14 and channel 12 and element 14 are arranged in housing 10 in a manner so that sensor 18 and channel 12 can be in fluid contact with each other when channel 12 is filled with a hydrating fluid 22.

Figure 2:
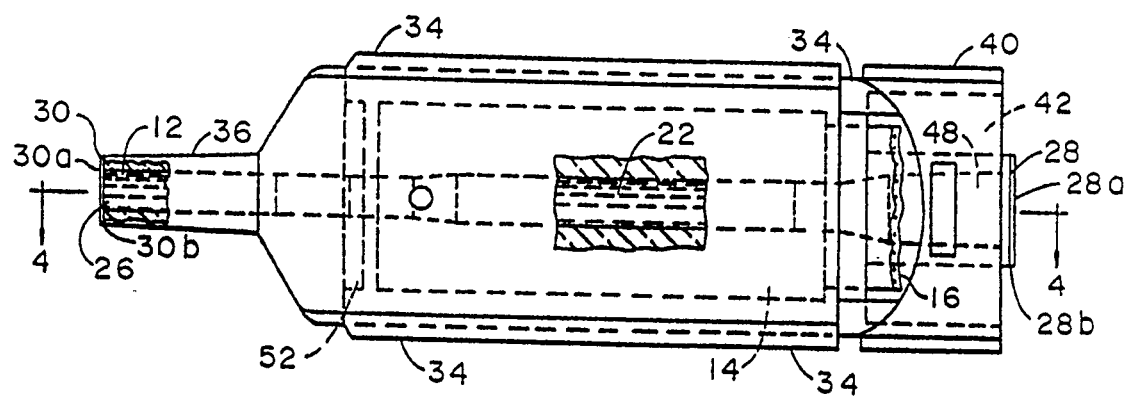
FIG. 2 is a bottom view of the housing of the sensor assembly taken alone line 2—2 of FIG. 1, where the channel contains fluid.

Housing 10 has at least one and preferably two openings, 24 and 26, arranged along channel 12 at different locations from each other in relation to sensor element 14. This arrangement allows hydrating fluid 22 that is subjected to fluid pressure from either opening 24 or 26 to flow across sensor element 14 and contact the one or more sensors 18. Channel 12 can have any shape that allows for laminar flow of fluid through it in the vicinity of the one or more sensors 18 along channel 12. Also, the openings 24 and 26 are sealed by a substantially moisture impervious seal 28 and 30, respectively. The opening 26 can serve as an inlet to or outlet from housing 10 that is preferably formed by conical tip 36. Also, the housing at the other end of the sensor element 14 from opening 26 can have a flared end 40 encompassing opening 24 that is formed by tip section 38, which preferably has a cylindrical exterior and a conical interior. The tip 38 is surrounded by flared end 40 which has an inner annular space 42 between the external rim 44 of the flared end 40 and the external surface of tip section 38. The openings 24 and 26 for housing 10 shown in FIGS. 1 and 2 are preferably aligned in the same plane and along the same axis at opposite ends of the channel 12 so channel 12 passes longitudinally through the housing along the same central axis. This arrangement provides sufficient support of the channel by the housing to receive and/or expel fluid through the channel with pressurized movement. Preferably, the sections 36 and 38 of housing 10 are at opposite ends of the housing 10 and contain portions of the channel 12 along with openings 24 and 26. The flared end 40 can also have one or more external ribs like 50 for ease of manipulation or handling of the housing 10. The attachment of sections 32 and 34 can be assisted by a guiding member and guiding slot shown together in FIG. 1 as 52

Figure 4:
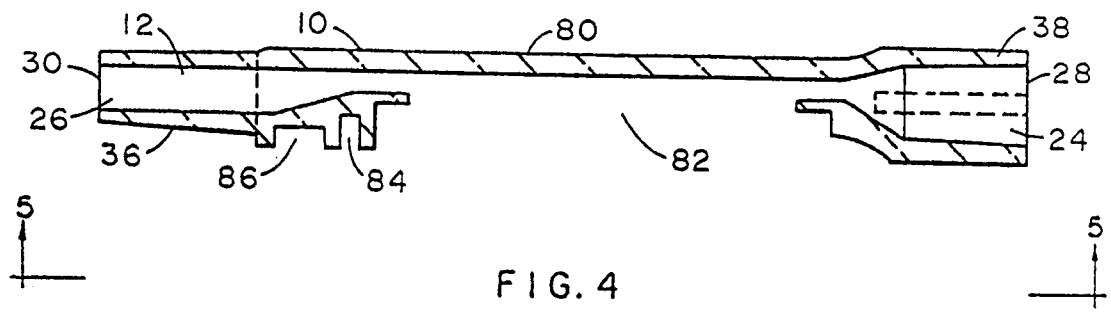
FIG. 4 is a side elevational of the first or top section of an alternative embodiment to that shown in FIG. 1 taken alone a line similar to that of lines 4—4 of FIG. 2 without the back portion of the sensor assembly and without the sensor board occupying the internal space.

Tip sections 36 and 38 allow for connection or coupling to a device to provide fluid pressure, rapid fluid flow, or suction to cause the fluid with an analyte, for example, to be measured to pass, preferably in non-capillary action or flow, in measuring contact with the one or more sensors 18. The tip section 38 distally located from tip section 36 can be similar to tip section 36 as shown in FIG. 4 or can be adapted and preferably is adapted to connect with a distal or needle-end end of a syringe. The distal end of the syringe fixedly engages the housing 10 through the annular space 42 and fixedly engages with the housing through attaching means 46 and 48. Preferably, the shape of tip 36 is of a standard outer diameter to allow for connection to sample gathering means or fluid withdrawing means such as needles or tubing or conduit from catheters or tubing in multi-sequential analyzing equipment. Most preferably, the shape is suitable for Leur attachment either slip or lok (lock) to a sample gathering means not shown in FIG. 1 such as a needle for a syringe.

Figure 5:
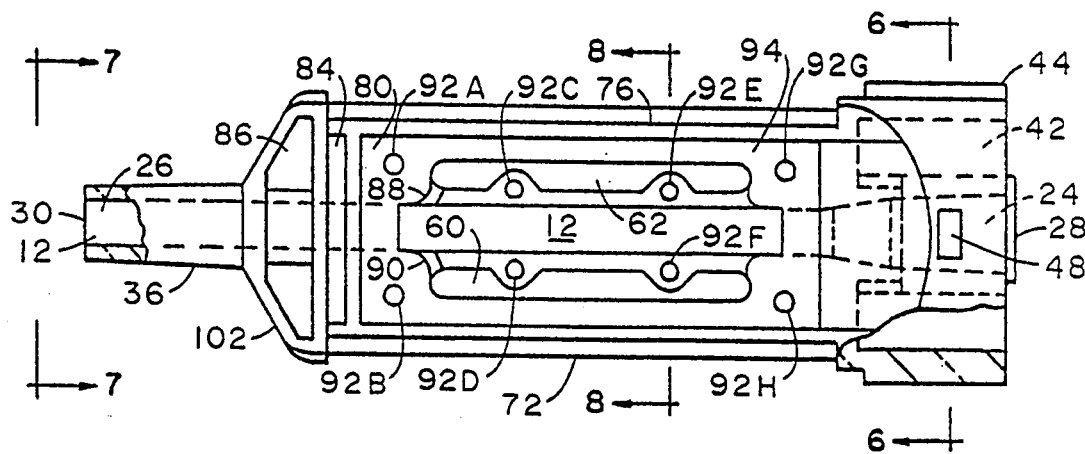
FIG. 5 is a bottom view of the housing taken along lines 2—2 of FIG. 1 without the back of the sensor assembly similar to that shown in FIG. 4.
Figure 7:
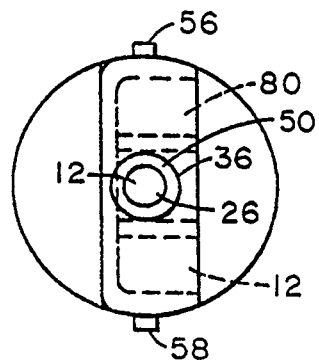
FIG. 7 is a forward end view of the housing.

Housing 10 preferably has one section 32 and another section 34 which have matched attachment means (not shown in FIG. 1 but shown in subsequent Figures) for connection to each other. Sections 32 and 34 fixedly engage to form the housing 10 having one or more internal spaces (a portion of which is shown in FIGS. 4, 5 and 7 as 82) for placement of sensor element 14. The internal space 82 need not be of any particular geometric configuration just so long as sensor element 14 fits into the space. The internal space 82 and sensor element 14 are preferably of matched configuration and are preferably generally rectangular. Preferably, one section 32 comprises a substantial portion of housing 10 as shown in FIG. 4 and the other section 34 is a cover for the back of sensor element 14 occupying internal space 82 of FIG. 4. With this arrangement and with the internal space 82 having dimensions that closely match those of the sensor element 14 for a snug fit of the latter into the former, the sections 32 and 34 can assist in providing electrical isolation between the hydrating fluid 22 and the electric circuit means 20. The former is at least in channel 12 and the latter is on sensor element 14. Preferably, section 32 has the tip sections 36 and 38 and all of the flared end 40 and forms a portion of channel 12 and any other channels that are present. The remaining portions of the channel 12 or other channels are formed by sensor element 14 occupying the internal space 82 so that the surface with one or more sensors as 18 actually forms a wall of the channel 12 as shown in FIG. 1. Any arrangement or configuration other than that shown in FIG. 1 can be used that allow the two sections 32 and 34 to engage and form housing 10 with one or more internal spaces for placement of sensor element 14 so that the sensor 18 is in fluid contact with hydrating fluid 22 that is in channel 12.

Similar numerals are used throughout the drawings to denote the same feature in each of the drawings. The bottom view of sensor housing 10 shown in FIG. 2 along lines 2—2 of FIG. 1 highlights the preferred matched configuration of sections 32 and 34 in a top and bottom relationship. Section 34 preferably matchedly engages section 32 through guide member and slot 52 of sections 34 and 32, respectively, shown better in subsequent drawings from the inner surface of bottom 34. In FIG. 2, the slot of 52 is shown in phantom as is channel 12 except for the cutaway portion showing hydrating fluid 22. Also shown in phantom is electrical cable means 16 as it enters housing 10. Slot 48 clearly shown in FIG. 2 provides for fixed attachment with a syringe not shown in FIG. 2 at the distal or outlet end of housing 10. Preferably, as shown in FIG. 2 an electrical insulating means 56 is present. The electrical insulating means 54 can be any material that can occupy spaces between housing sections 32 and 34 and sensor element 14 other than the one or more channels and electrical attachment means 16 to assist in providing for electrical isolation. The insulation can restrict any contact between any hydrating fluid 22 and the electric circuit means 20 to reduce the possibility of any short circuits or leakage current. This material should have the following characteristics: an insulation factor of around $10^{14}$ ohms/cm$^2$ and substantially impervious to moisture and preferably curable at a temperature of less than around 60 degrees Centigrade. Nonexclusive examples of a suitable material include: epoxy polymer, modified epoxy molding compound such as brominated epoxies, epoxy molding compounds, polyimides, unmodified polyimides like PMDA-ODA and BTDA ODA-based polyimides, Poly(amide-imide) polymers, modified polyimides having modification from diamic acid additives, siloxane polyimides, and high temperature polymers like silicone polymers, and polyarylene ether polymers. A particularly suitable material is a bisphenol A epichlorohydrin type epoxy polymer like that available from the Hysol Division of The Dexter Corporation in Industry, Calif. 91749 under the trade designation EE4207.

Seals 28 and 30 FIGS. 1, 2, 4 and 5 can be and preferably are substantially impervious to air, and they may be comprised of a single layer or multilayer laminate. A suitable single layer material includes metal foil that is capable of sealing by a polymeric material that can be heat-treated or RF (radio frequency) treated for sealing. The multilayer laminate material ordinarily has an interior layer of polymeric material and outside this layer a metal foil layer. A typical laminate can have two or more layers and may have an additional outer polymeric layer to facilitate abrasion resistance or printing on top of the metal foil layer. A non-exclusive example of the metal foil is aluminum. A three layer laminate suitable for the seal of the present invention can have from the exterior surface to the interior layer the following: 1) nylon, polyester, polyethylene or polypropylene, 2) aluminum foil, and 3) an inner heat sealable polymeric layer such as polyethylene, polypropylene, polyvinylidene chloride or nylon. A nylon-foil-polypropylene laminate of, i.e., 17 grams per square meter nylon, 32 grams per meter squared aluminum, 45 grams per meter squared polypropylene or of a suitable example is a polyfoilpolylaminate which is a three-layer composite having an aluminum foil intermediate layer and an inner and outer layer of polypropylene. The seals are puncturable and preferably can and form a seal that can withstand gamma radiation sterilization. The seals preferably have at least two sections—one section 28a and 30a away from the mouth or opening of the channel and another section 28b and 30b in contact with the housing 10 to seal the openings 24 and 26, respectively of the channel 12. The "a" seal sections can be at least an air impervious metal foil, preferably aluminum, and the "b" seal sections can be an adhesive material. Preferably, the seals 28 and 30 are a paper-backed aluminum foil coated with a clear heat sealable coating. The coating can be a blend of a high molecular weight ethylene and vinyl acetate copolymer. A nonexclusive example of a suitable material is an aluminum foil having a heat seal polyester film available under the trade designation "Foilseal 3-6" available from Selig Sealing Products, Inc. 17w745 Butterfield Road, Oakbrook Terrace, Ill. 60181. Such materials can have a gas transmission for oxygen that is nil and a water vapor transmission which ranges from around 0.005 to 0.059 GS (grams)/CSI(100in$^2$)/24 hours at 90 percent relative humidity. Such materials provide a seal that when securely attached across the openings 24 and 26 of the channel 12 provide substantial imperviousness to air. These values are obtained on a Permatran-W6 for water transmission and an Ox-tran 1000 for oxygen transmission, and both pieces of equipment are available from Mocon, Modern Controls, Inc., 4220 Shingle Creek Parkway, Minneapolis, Minn. 55430. The thickness of the seals 28 and 30 can range from an overall thickness of around 1 to around 10 mils with the heat seal coating ranging in thickness from around 0.5 mil to around 4 mils and more preferably from around 0.5 to around 2 mils and the aluminum foil ranging in thickness from around 0.1 to around 8 and more preferably from around 0.3 to around 2 mils.

Figure 6:
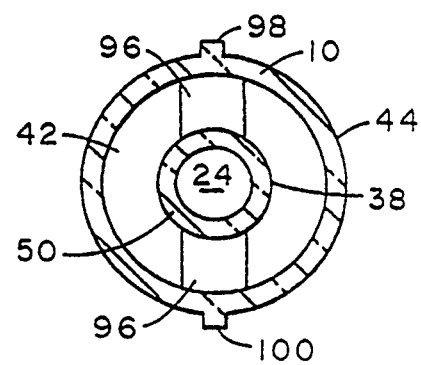
FIG. 6 is a sectional view of the distal end of the sensor assembly taken along lines 6—6 of FIG. 5.

Alternatively, seals 28 and 30 can have an adhesive material as the "b" section which is a thermoplastic resin suitable for hot melt deposition or extrusion lamination. Suitable examples of these thermoplastic resins include resins known as the so-called hot-melt type adhesive, such as polyethylene, an ethylene/vinyl acetate copolymer (EVA) or a partially saponified EVA. For instance, a graft copolymer can be used that is a 20 to 60 percent saponification product of an ethylene/vinyl acetate copolymer (EVA) having a vinyl acetate content of 15 to 45 percent by weight as a trunk polymer and a polymer of an unsaturated carboxylated acid in a quantity of 0.1 to 10 percent by weight of the partially saponified EVA as a branch polymer. Also, the seals 28 and 30 can be a composite of an aluminum/polypropylene film with a heat sealable resin such as a polyamide, polyolefin, and saturated polyesters. When sealing to adhere the resin to the plastic surface and thereby adhere the seal to channel 12 is performed by heat sealing, any induction sealing or any heat sealing method known to those skilled in the art can be used. The method of sealing depends to a degree on any securing means used to maintain the seals 28 and 30 in a snug relationship to the tips 38 and 36, respectively 18. The seals 28 and 30 can have any shape suitable for covering completely openings 24 and 26 and providing for a snug fitting with the flat surface of the rims 50 as shown in FIGS. 6 and 7 of the tips 36 and 38. Preferably, the seal is in the form of a disc having a diameter similar to the diameter across the opening and tip for attachment to the tip rim to cover the opening 24 and 26.

Figure 3:
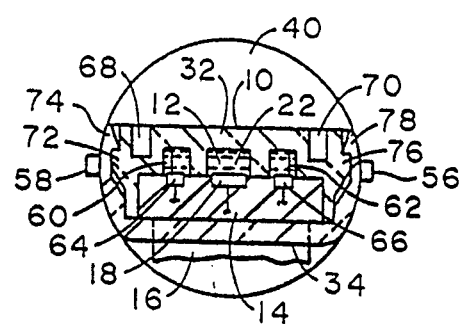
FIG. 3 is a sectional elevational view of the sensor assembly along lines 3—3 of FIG. 1.

The sectional elevational view of the sensor apparatus shown in FIG. 3 is along lines 3—3 of FIG. 1. As shown in this figure, on housing 10 ridges 56 and 58 can be present for ease of handling. Flared end 40 is shown from this view from the front of the apparatus. The electrical attachment means 16 is shown as a cable extending from the bottom of housing 10. This view shows the preferred embodiment of the invention having a plurality of channels. In addition to channel 12, the housing 10 and sensor element 14 forms two additional channels 60 and 62 which also can and preferably do contain hydrating fluid 22. As shown in FIG. 3, channel 12 is in fluid contact with sensor 18 which is on sensor element 14. Also shown in fluid contact with channels 60 and 62, respectively, are electrodes or sensors 64 and 66. Also as shown in FIG. 3 there may be and preferably are present two longitudinal slots 68 and 70 which are in the top section 32 of housing 10. These slots are for mold enhancements for plastic molding of the housing 10 to assist in obtaining flat external and internal surfaces for a larger housing section 32. The ridges 56 and 58 are on housing section 34 which securely fastens to housing section 32 by matching fastening means 72 on top section 32 and 74 on bottom section 34. Mirror image fastening means are present on the opposite side of housing 10. These fastening means can be on the sides of housing 10; one on each interior side of bottom section 34 and two on the top section 32 of housing 10 where one is on each side of housing 10.

In FIGS. 1–3 and the remaining figures, the sensor element 14 can have one or more sensors like sensor 18 having one or more hydratable membranes known to those skilled in the art. Preferably, sensor element 14 is a nonconducting substrate with electrical circuitry 20 electrically connected to at least one sensor through at least one electrode. Generally, the nonconducting substrate can be a glass or ceramic including sheet or chip or nonconducting substrate like nonconducting polymers or commercially available frit that can be used as the substantially smooth flat surface for the nonconducting substrate. Nonexclusive examples include borosilicate glass as is known to those skilled in the art for producing thick film or layered circuits. A nonexclusive but preferred example of which includes a ceramic base having around 96% A1203 such as that available commercially from Coors Ceramic Company, Grand Junction, Colo. Generally the electrical circuitry 20 is any electrical circuit means known by those skilled in the art. Both the sensor 18 and the electrical circuitry 20 can be prepared from any number of well known layered circuit or integrated circuit technologies, as for example, thick film, thin film, plating, pressurized laminating and photolithographic etching, and the like, however, the thick film technique is preferred. A suitable sensor element is that described in the allowed U.S patent application Ser. No. 07/343,234, filed on Apr. 26, 1989, U.S. Pat. No. 5,046,496 and titled, "Sensor Assembly for Measuring Analytes in Fluids, which is commonly assigned, and which is incorporated herein by reference. The at least one sensor 18 can be a potentiometric or amperometric sensor, in that the former has one electrode and the latter has two, both an anode and a cathode. In the situation where the sensor 18 is potentiometric, an additional electrode is usually present as a reference electrode. Any reference electrode known to those skilled in the art can be used. The potentiometric or amperometric sensor preferably has a hydrophilic polymeric membrane and the sensor preferably has an aqueous-based electrolyte with suitable ionized chemical species like those in silver/silver chloride, calomel and mercury sensors or electrodes. Suitable examples of such membranes that may be present in electrochemical sensors for use in determination of blood gases are described in U.S. Pat. Nos. 3,088,905; 3,912,614; 4,133,735; and 4,454,007 and European patent specifications 0015075 and 0027385 and the article in the Journal entitled "Medical and Biological Engineering Computing", 1978, Vol. 16, pages 599–600. The publications describe blood gas detectors requiring the presence of membranes and a number of useful or potentially useful membrane materials. Suitable nonexclusive examples of a hydrophilic polymeric membrane include polyvinylchloride and modified polyvinylchloride and any similar hydrophilic hydratable polymeric membrane known to those skilled in the art.

Figure 18:
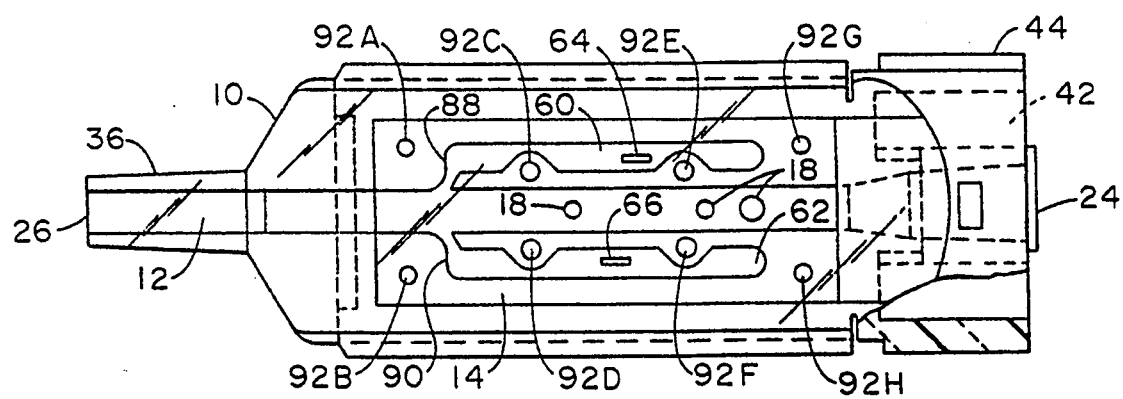
FIG. 18 is a top plan view of the housing of the sensor assembly taken along line 2—2 of FIG. 1, where the channel does not contain any fluid.

In addition to channel 12 having fluid contact with a sensor, sensor 18 on the substrate of sensor element 14 as shown in FIG. 3, the sensor assembly of the present invention may have a plurality of channels. The arrangement of the channels and the sensors is such that when a plurality of channels and a plurality of electrodes for the sensor or sensors are present at least one channel can be in fluid contact with at least one sensor. With this type of arrangement, the one or more side channels are in fluid contact with at least channel 12 or with another channel connected to channel 12 so that each of the one or more side channels can provide fluid contact with the at least one electrode associated with that channel. This sensor or electrode to channel relationship is shown in FIGS. 3 and 18, while the channel to channel relationship is shown in FIG. 5. In FIG. 3 channels 60 and 62 are formed by the one housing section 32 and the adjacent positioning of sensor element 14 in the internal cavity or space formed by the joined two housing sections 32 and 34 in a fashion similar to the aforementioned formation of channel 12. Sensors or electrodes but preferably reference electrodes 64 and 66, respectively, are in contact with channels 60 and 62. Preferably, these channels contain fluid like hydrating fluid 22 as contained in channel 12 or any fluid known in the art to act as an electrolyte for the reference electrode. Preferably, the potentiometric and/or amperometric sensors are located in channel 12 and only the reference electrodes are located in the one or more additional or side channels 60 and 62 and most preferably each reference electrode is located in a separate side channel as shown is FIG. 18.

The electric circuitry 20 is shown in FIG. 3 by line 20, which connects to electrical attachment means 16 preferably by a cable 16 electrically connecting to the nonconducting substrate of sensor element 14. Cable 16 can be any suitable electronic multiple conductor with suitable leads to carry analog signals and preferably not binary signals. Preferably the cable is a ribbon-type cable with a plurality of wires in one tape-like strip to provide the sensor element 14 with electrical communication from the at least one sensor 18. The connection of the electrical circuit means or cable 16 to the nonconducting substrate of 14 is in a manner to communicate electrically with at least the one or more sensors or electrodes but to avoid contacting the hydrating fluid 22 which may cause short circuits or current leakage.

The hydrating fluid 22 is any liquid suitable for maintaining the membrane of sensor 18 in a non-dried state. For instance, the liquid will have some amount of water although a minor quantity of organic liquids may also be present. Preferably, the liquid is a stable liquid for storage ranging from a short time (days or weeks) to prolonged periods of time of several months. Preferably, the liquid is an aqueous solution that is isotonic with any electrolyte in the one or more sensors. More preferably, the hydrating fluid 22 is also isotonic to act as the electrolyte for any reference electrodes that may be present on the sensor element 14 as reference electrodes 64 and 66 as shown in FIG. 3. A suitable example of a hydrating fluid is an aqueous solution comprising: disodium hydrogen phosphate, potassium dihydrogen phosphate, sodium bicarbonate, and sodium chloride. Such a solution can have a varying range of amounts for the individual constituents but most preferably for the aforelisted salts the amounts are in millimoles per kilogram of water in the order listed as follows: 4.8, 13, 22, and 12.5. The quantity of hydrating fluid in channel 12 or the plurality of channels is at least that which is sufficient to cover or remain in contact with the one or more sensors. For example, seals 30 and 28 of FIGS. 1 and 2 could be in channel 12 rather that at the opening so as to maintain the hydrating fluid 22 in contact with the one or more sensors. In this situation the seals 28 and 30 would be more plugs rather than foil-backed seals.

FIG. 4 shows an alternative embodiment of housing 10 to that depicted in FIGS. 1 and 2 in that tip section 38 is a mirror image or near mirror image of tip section 36 at the other end of the housing. Hence, the difference between the embodiment of FIG. 4 and that of FIG. 1 is that the housing 10 with the near mirror image of tip sections 36 and 38 does not have the flared end 40 of FIG. 1. FIG. 4 is a side section without the back portion 34, the sensor element 14, and electrical attachment means 16 as shown in FIG. 1 and the electrical insulating means 54 shown in FIG. 2. FIG. 4 has at least one channel 12 with openings 24 and 26 sealed by seals 28 and 30. With this view the internal space 82 is shown where sensor element 14 is placed. Since the sensor element 14 can have any geometric shape, the internal space should be of a matching shape to accommodate the sensor element and to minimize the possibility of gaps that would allow hydrating fluid to leak into contact with the electrical circuit means 20 or cable 16. Also shown in FIG. 4 is the slot 84 which is a portion of the slot and tab assembly shown in FIG. 1 as 52. This slot assists in aligning the attachment of back 34. As shown in FIG. 2, the slot runs transversely across the bottom of the upper section 32 of housing 10. In addition the void space 86 of FIG. 4 can be present or absent depending on the molding process for producing the sensor assembly.

FIG. 5 is another bottom view taken along a transverse line 5—5 of FIG. 1. Here, internal space 82 is of adequate dimensions to hold a comparably dimensioned sensor element (not shown) to completely fill the space to provide walls for not only channel 12 but also channels 60 and 62. Preferably, channels 60 and 62 are joined to channel 12 through joining sections 88 and 90. As an alternative embodiment, although not shown in FIG. 5, similar joining sections can be present at the other end of channels 60 and 62 connecting to channel 12. The difference between channels 60 and 62 and channel 12 is that the former are side channels which do not flow through the housing 10 but are joined for fluid flow to the main channel 12. The diameters of the channels can be the same or the diameter of channels 60 and 62 can be smaller than that of channel 12.

As shown in FIG. 18 the plurality of channels preferably associate with the electrodes and sensors so that the one or more sensors 18 of sensor element 14 are positioned in channel 12, while other sensors or electrodes 18 are on sensor element 14 for positioning in side channels 60 and 62. With this arrangement it is preferred that sensors for measuring the partial pressure of oxygen and electrodes or sensors for measuring the partial pressure of carbon dioxide and for measuring pH are in channel 12, while channels 60 and 62 each have a reference electrode 64 and 66, respectively. When hydrating fluid 22 is in the channels, the fluid in channel 12 is more easily displaced with the sample fluid to be measured relative to the fluid 22 in channels 60 and 62. Therefore, reference electrodes 64 and 66 are measuring as a reference a known fluid for comparison for the measurement of the sample fluid in channel 12.

The housing 10 has a plurality of attachment ports to assist in holding the sensor element 14 in place in the internal space 82 and to assist in attachment between top section 32 and bottom section 34. The preferred rectangular shape of internal space 82 is shown in FIG. 5. The number of ports can range from around 2 to around 8 although higher numbers can be present and the ports can range in geometric configuration from circles to slots to square and the like for mechanical or chemical attachments. The mechanical attachments can be plastic or metal rivets or fasteners like screws and the chemical attachment can be adhesives, preferably curing adhesives such as a UV-curing adhesive. FIG. 5 shows eight ports (92A-92H). The preferred number of eight ports are arranged such that two of the ports, 92C and 92E, are positioned between channel 12 and side channel 62 and two ports, 92D and 92F, are positioned between main channel 12 and side channel 60. The other four ports are located outside of the channel array and preferably near the corners of the internal space 82 so that ports 92A and 92B are at the two corners of one end of internal space 82 and ports 92G and 92H are located at the other two corners of internal space 82. The ports extend from the internal surface 94 of housing member 32 to the external surface 80 shown in FIG. 4 of housing section 32 to provide for placement of the attachment means from the outside or external to housing 10 and into the internal space 82 when it contains the sensor element 14.

Also shown in FIG. 5 is inner annular space 42, in phantom, slot 48, opening 24 and seal 28. At the distal end of the housing 10, the tip 36 is shown with a partial cutaway showing channel 12 that is sealed with seal 30 over opening 26. Also a void 86 is shown in FIG. 5 which is present to decrease the amount of material used and to reduce the weight of the sensor assembly. The void 86 can extend completely through the housing sections 32 and 34, respectively, of housing 10. The attachment means of member 32 for engagement with member 34 are shown in FIG. 5 at 72 and 76 as longitudinal ridges along the exterior sides of the planar portion of housing member 10.

FIG. 6 is a sectional view of the proximate end of the sensor assembly showing opening 24 of channel 12. The channel extends into the flared end section 40 of the sensor assembly to form tip 38 for channel 12. Between tip 38 and rim 44 of flared end 40 is the inner annular space 42. Extending beyond annular space 42 into housing 10 in the direction of internal space 82 is detent 96 on both external sides of tip 38 for formation of the more or less planar portion of housing 10. Extending outwardly from and normal to the peripheral surface of flared end 40 are projections 98 and 100. These projections extend outwardly a short distance and preferably in the same plane so they continue along the same longitudinal axes of housing 10 as ridge members 56 and 58 shown in FIG. 3. These projections assist in handling of the sensor assembly when it is connected to a syringe (not shown). As previously discussed, the inner annular space 42 accepts a Leur fitting for attachment as depicted in FIG. 6 to a conventional syringe.

FIG. 7 shows the distal end of sensor housing 10 in a sectional view. The tip section 36 provides a housing for channel 12 which has opening 26 at this distal or receiving end. Also shown are ridges 56 and 58 which extend from housing 10. As mentioned for and shown in FIG. 6, the projections 98 and 100 are extensions of these ridges since FIGS. 6 and 7 are the opposite ends of the housing 10 rotated in the same horizontal plane 180°. The internal space 82 is shown above and below and to one side of channel 12. Tip section 36 extends beyond the shoulder region 102 of the essentially planar section of the housing 10 as shown in FIG. 5.

Figure 8:
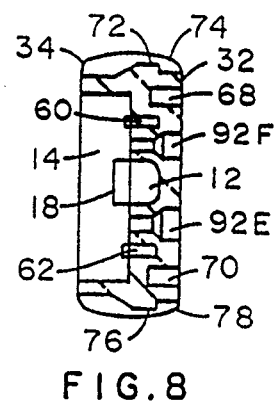
FIG. 8 is a sectional view through the sensor assembly taken along line 8—8 of FIG. 5.

FIG. 8 shows a sectional view along line 8—8 of FIG. 5 of the housing section 32 of the sensor assembly. Member 32 has a portion of internal space 82 which is completed upon attachment of housing member 34 as shown in FIG. 1. FIG. 8 is rotated 90° in the clockwise direction in the same plane in regards to FIG. 3. Also shown are fastening ports 92F and 92E. The fastening ports are interspersed one above and one below channel 12. Above port 92F and below 92E are secondary channels 60 and 62, respectively. Fastening means 72 and 76 of housing member 32 are shown in engaged fashion with fastening means 74 and 78 of housing member 34 for engagement of the two housing members 32 and 34. Another section of the slots 68 and 70 that extend longitudinally along the exterior surface of housing member 32 as depicted in FIG. 4 as 80 is shown in FIG. 8.

Figure 9:
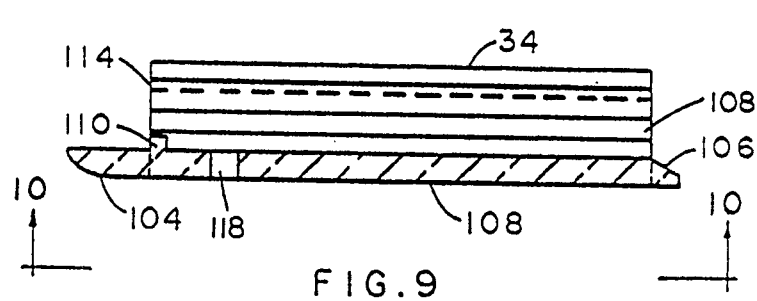
FIG. 9 is a front sectional elevational view of the back portion of the sensor assembly.
Figure 11:
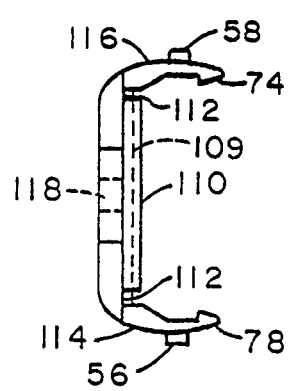
FIG. 11 is a forward end view of the back portion taken along lines 11—11 of FIG. 9.
Figure 10:
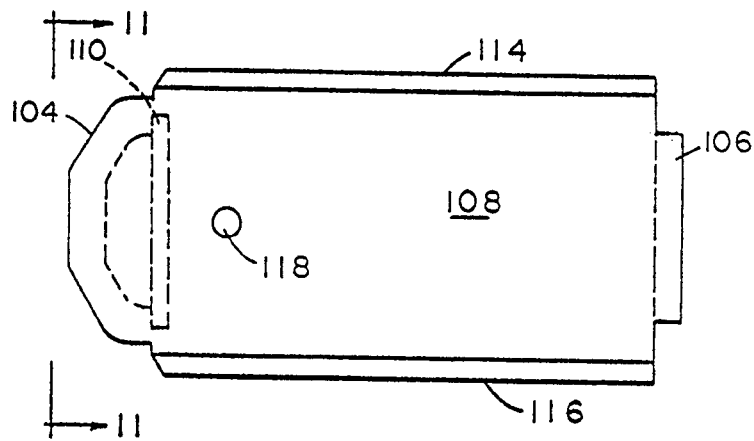
FIG. 10 is a bottom view of the back portion taken along lines 10—10 of FIG. 9.

FIGS. 9, 10 and 11 show the housing member 34 of the sensor assembly.

FIG. 9 is the side section elevational view of the back portion of the sensor assembly 10 having a tongue section 104 which when attached to member 32 covers void space 86 as shown in FIG. 5. When housing members 32 and 34 are attached, tongue 104 conforms to the shape of the shoulders 102 of the upper section as more clearly shown in FIG. 10. Also, lip 106 extends from the exterior surface 108 of housing member 34 so that when member 34 engages member 32 a slot-like opening is available for cable attachment means 16 for electronic communication of the sensor assembly. Tab 110 is for mating attachment to slot 84 of housing member 32. Tab 110, which is a portion of assembly 52 shown in FIG. 1, projects preferably at around a 90° angle from the interior surface 112, shown in FIG. 11 of member 34. The tab slidably engages or fills slot 84 which both traverse the longitudinal axis of members 34 and 32, respectively, as a guide for engagement of these members. Of course, the tab and slot arrangement can be any guiding mechanism arranged in any fashion and at any location on members 32 and 34 to assist in their engagement as long as there is no interference with the sensor element 14.

The tab 110 and slot 84 and lip 106 for the cable slot are preferably located where shown in the Figures. This arrangement allows for the cable attachment means 16 to associate with the housing 10 at or near the proximate end of the housing and travel to around the distal end of the housing for attachment to the electric circuit means 20. This way the cable can travel a substantial distance of the longitudinal axis of the internal space 82 to retard the loss of heat from the sensor element 14 through the cable.

As shown in FIG. 9, member 34 has a side element laterally extending at around a 90° angle from each side of internal surface 112 of member 34. One of these sides is shown in FIG. 9 as 114, while a mirror image laterally extending side 116 is behind side 114 in FIG. 9 as shown in FIG. 11. The laterally extending sides 114 and 116 extend in connecting fashion to engage the housing member 32 preferably on its lateral sides. As shown, lateral side 114 has a ridge which is ridge 56 of FIG. 3 that travels the longitudinal axis of the lateral side and that extends outwardly preferably at an angle of around 90° from side 114.

FIG. 10 is a bottom view of member 34 taken along lines 10—10 of FIG. 9 showing tongue member 104 and lip member 106 both beginning at one lateral side and extending transversely almost or to the other lateral side. In addition, hole 118 is in the back for insertion of chemical electronic insulation means 54. Tab 110 is shown in phantom and the laterally extending sides are approximately normal to the plane of exterior surface 108.

As shown in FIG. 11, a forward end view of member 34 taken along lines 11—11 of FIG. 10, tab 110 projects laterally and approximately normal to the plane of surface 108 in this view. The laterally extending sides 114 and 116 each have the attachment means 74 and 78 to matchedly engage the attachment means 72 and 76, respectively, on member 32. Also, the ridges 56 and 58 are shown extending from laterally extending sides 114 and 116, respectively. Also shown in phantom is hole 118.

Figure 12:
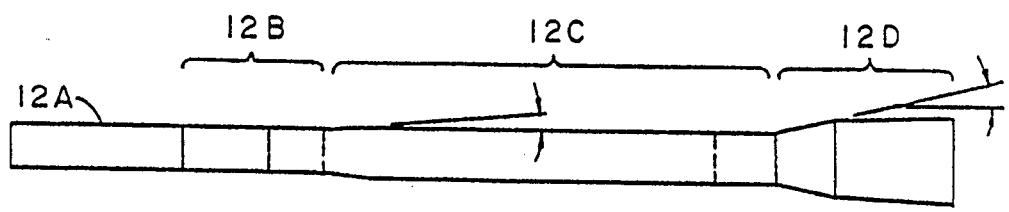
FIG. 12 is a front elevational view of the contour of the channel formed along the longitudinal axis on the interior of the housing.
Figure 13:
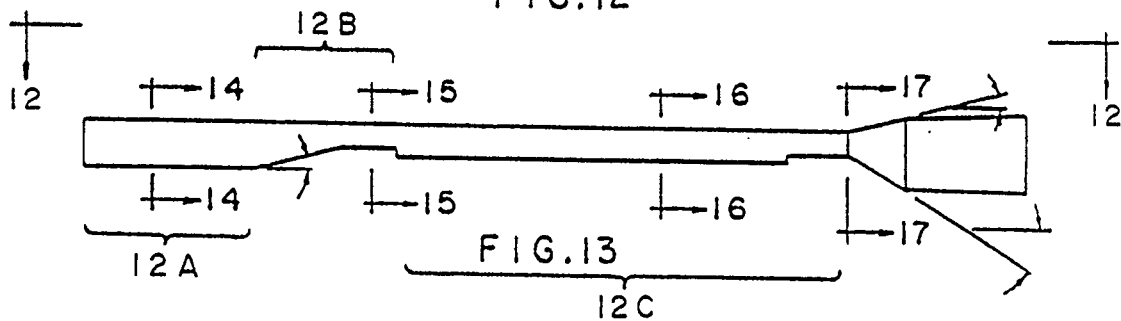
FIG. 13 is a top view of the contour of the channel taken on line 13—13 of FIG. 12.

FIG. 12 shows channel 12 as it longitudinally passes through housing 10 in a plan elevational view of the contour of channel 12 formed along the longitudinal axis on the interior of the housing. The contours shown in FIGS. 12 and 13 are depicted in phantom and FIGS. 1 and 2, respectively. FIG. 12 is a top view of the channel taken on lines 13—13 of FIG. 13. The 12a portion indicates that portion of the channel passing from the tip 36 in FIG. 1. Portion 12b is that part of the channel which passes through the shoulder section, 102 of FIG. 5, of housing 10 into the interior cavity. Portion 12c is that part in the internal space 82 of housing 10 formed from housing member 32 and the sensor element 14 occupying space 82 in between top member 32 and bottom member 34. Preferably, cable attachment means 16 is in between sensor element 14 and housing member 34. Portion 12c preferably has a wider diameter than that of 12a or 12b although it could have the same diameter. Portion 12d is that section of the housing enclosed by tip 38 passing from the internal space 82 into the flared end 40 of the housing. This portion preferably has a wider diameter for coupling to a fluid collection pressure device such as a syringe.

Figure 14:
FIGS. 14–17 is a cross sectional view of the channel at various portions along its length.
Figure 15:
Figure 16:
Figure 17:

The side elevational view of FIG. 13 again shows portion 12a, where a cross section along line 14—14 is shown in FIG. 14. As shown in FIG. 14, the channel at this location has a circular cross section and is the portion formed by the tip 36. As shown in FIG. 13, the slope of the bottom of the channel increases as the bottom ascends to the bottom level as shown in FIG. 13 around the cross sectional line 15—15. The cross sectional view shown in FIG. 15 along a line 15—15 in FIG. 13 details a flat bottom portion of the channel for a portion of 12b. Here, the channel has a flat bottom as the channel 12 enters the planar section of the housing 10. Portion 12c extends along the longitudinal axis of the planar section of the housing and has a cross section as shown at FIG. 16, which is along line 16—16 of FIG. 13. At cross sectional line 17—17 of FIG. 3 the bottom is notched by the detent 96 of FIG. 6 to provide for coupling to the device like a syringe. After the point in FIG. 13 at line 17 the diameter of the channel widens again. The constriction and widening of the diameter of the channel is for the purpose of obtaining an opening that is a minimum diameter for accepting a standard Leur fitting like that on a syringe. The portion of the channel shown in FIG. 13 is that which is preferably formed by the housing section 32. Preferably, the other housing section 34 forms little, if any, of the portion of the channel 12. The beginning of portion 12d has the cross section shown in FIG. 17 just as the channel exists the planar section into the flared end section 40 of the housing 10. A cross section of the end of the channel 12 is shown in FIG. 6 formed by the tip 38.

The sensor assembly is prepared by placing the sensor element 14 with one or more sensors 18 having unhydrated membranes, preferably three sensors, one for measuring the partial pressure of oxygen, another for measuring the partial pressure of carbon dioxide and a third for measuring the pH of fluids, preferably fluids like blood. The sensor element 14 is placed in the internal space 82 of housing member 32 as shown in FIGS. 1, 2, 4 and 5. The electrical attachment means 16 is electrically connected to sensor element 14. When the sensor element 14 is placed in internal space 82, this electrical connection is preferably at the distal end although it could be at the proximate end of housing 10. The cable stretches along the length of the sensor element 14 between the element 14 and the housing member 34 and exits housing 10 at the near proximate or exiting end 40. The attachment of the cable 16 to the nonconducting substrate of the sensor element 14 can be by any attachment means known to those skilled in the art for attaching cables to substrates for electronic circuits. Additionally, it is preferred to have a foam pad shown as 109 in FIG. 11 between the electrical attachment means 16 and housing member 34 so that there is uniform compression of sensor element 14 to the bottom of housing section 32. Housing member 34 is aligned with housing member 32 through the tab-and-slot arrangements 110 and 84 and preferably snapped through attachment means 72, 74, 76 and 78 as shown in FIG. 8.

An adhesive that is curable by ultra-violet light is placed in at least some of the ports 92a through 92h and also preferably along the interior surface of the housing member 32 by wicking. Any suitable adhesive known to those skilled in the art of joining polymeric parts to glass or ceramic substrates can be used, but it is preferred to use an ultraviolet light curable adhesive that is substantially water insoluble in the cured state. A nonexclusive example of a suitable material is the UV curable epoxy adhesive P/N 10033 available from an electronic materials vendor. Also this adhesive may be used with about 0.005 percent by weight polychrome blue organic dye to highlight the details of the adhesive. Before placing the housing with the adhesive in a UV-curing zone to cure the adhesive, it is preferred to allow the adhesive to wick within the internal opening 82 along the surface of housing member 32. The wicking of the adhesive within the cavity is preferably on both sides of the side channels. Preferably, the quantity of adhesive that is used allows for wicking lengthwise along the bottom of section 32 on both sides of channel 12 and under the channel so the bead of adhesive is near continuous on both sides of the channel 12. The curing can occur in any commercially available UV-curing oven with or without a conveyor. After curing the wicked adhesive, the housing 10 is cooled to ambient temperature. Preferably, now the UV-adhesive cured by ultraviolet light is placed in the ports and again placed in the UV-curing oven.

After the joining of the housing members with the adhesive, the electronic isolation means, preferably an epoxy, that is cured at room temperature and atmospheric pressure is filled through hole 118 in member 34 as shown in FIG. 10 into the internal space 82 that is not already occupied. To increase the rate of cure, the housing is preferably placed and maintained in an oven for about two hours at 60° C. After the electronic insulating material has hardened or cured, as in the case of an epoxy material, the housing 10 can be pressure tested at an air pressure of around 10 to around 15 psi.

Upon joining of the housing members to contain the sensor element 14 and cable 16, one opening of the channel 12 is sealed which can be either opening 24 sealed with seal 28 or opening 26 sealed with seal 30 by a heat sealing but preferably an induction sealing process. After the sealing of one end, the hydrating fluid is added to channel 12 and any side channels to fill substantially all of the channels although small amounts of air bubbles can be tolerated in the channels but preferably the channels are filled to capacity. The remaining opening of the housing is sealed with the other seal through a heat sealing process but preferably an induction sealing process.

The sealing of seals 28 and 30 to channel 12 at the top and essentially flat rim portion 50 in FIGS. 6 and 7 depends on the presence or absence of any mechanical attachment means such as caps or the like and the type of thermoplastic adhesive polymer 24. When the cap is present, either the heat or induction sealing process can be used and any cap known to those skilled in the art for covering an opening in a plastic vessel can be used such as a screw cap or a snap cap. With the use of screw or snap caps, the seals 28 or 30 can be placed in the cap, and the cap applied to one of the openings 24 or 26 of the channel 12. When the cap is absent, induction sealing should be used to avoid the escape of any hydrating fluid (gas) from or the influx of gas into the channel 12. In general, the sealing needs to overcome the hurdle of adhering the seal to a plastic or polymeric substrate in a possibly moist environment since there may be moisture or liquid on the surface of tips 36 and 38 after the addition of the hydrating fluid.

With the capped channels a plurality of housings 10 can be heat or induction sealed. The heat sealing temperature and the pressure applied by the cap can vary depending on the type of heat sealable resin that is used with seals 28 and 30. In general, however, sufficient results are obtained by conducting the heat sealing at a temperature higher than the softening or melting point of the heat sealable resin and the pressure is sufficient if it doesn't cause excessive or substantial flow of heat sealable resin away from the area to be sealed. For heat sealing of a polypropylene heat sealable resin, the seal pressure by the screw-type cap is in the range of 2 to 5 kilograms per centimeter$^2$ (Kg/cm$^2$) for the temperature of heat sealing in the range of 180° C. to 280° C. For a polyamide, like Nylon 12, heat sealable resin the pressure is in the range of 2 to 7 Kg/cm$^2$ for the temperature of sealing of around 200° C. to 300° C. For polytetramethylene terephthalate the seal pressure is around 2 to 7 Kg/cm$^2$ for the sealing temperature in the range of 220° C. to 320° C. The time required for heat sealing varies depending on the thickness of the heat sealable resin layer.

Generally, the heat sealing is conducted for a time sufficient to perform melting and bonding of the sealable resin, for example 0.1 to 5 seconds. The heat sealing operation can be performed in an operation comprised of one stage or two or more stages. In the latter case, the same or different temperature and pressure conditions as those aforementioned can be adopted at these stages. The formed sealed area is cooled, if necessary, under application of pressure by optional means to form a sealed area with good sealing efficiency. For instance, immediately after completion of the heat sealing operation, the heat sealed area in which the resin is still in the softened or molten state is pressed by two positively cooled press bars whereby the resin is solidified. Although any operation known to those skilled in the art to cool and harden the adhesive polymer can be used.

For induction sealing, generally any induction sealing process known to those skilled in the art of induction sealing can be used. A nonexclusive example of a suitable process involves placing the housing 10 with seal 28 or 30 in place over the opening 24 or 26, respectively, of the channel 12 on the flat surface of the rim 50 of one of the tips 36 or 38, respectively. With the seal in place over the opening, that end of the housing with the seal over the opening is held with the application of pressure against a region where it is exposed to high-frequency electromagnetic waves. A suitable piece of equipment is that available from Giltron, Inc., Medfield, Mass. 02052, referred to as Foil Sealer Induction Heat Sealer, Model PM1. The aluminum foil of the seal is locally heated to a point whereby it heats and melts the adjacent resin layer. The melted resin layer adheres to the top horizontal surface of the rim of the tip that surrounds the opening. The hydrating fluid is placed in the channel in the aforementioned manner and the other seal is placed over the other opening at the other tip and subjected to induction heating in the same manner to seal the other end.

When the sensor assembly needs to be sterilized, the sensor assembly with the sealed channel can be sterilized by gamma-sterilization or pasteurization sterilization. A nonexclusive example of a pasteurization technique that can be used with the sterilizable container of the present invention is heating one or more of them at a temperature of around 70° C. for eight hours. The gamma-radiation sterilization can occur with the use of any gamma-sterilization equipment known to those skilled in the art.

Figure 21:
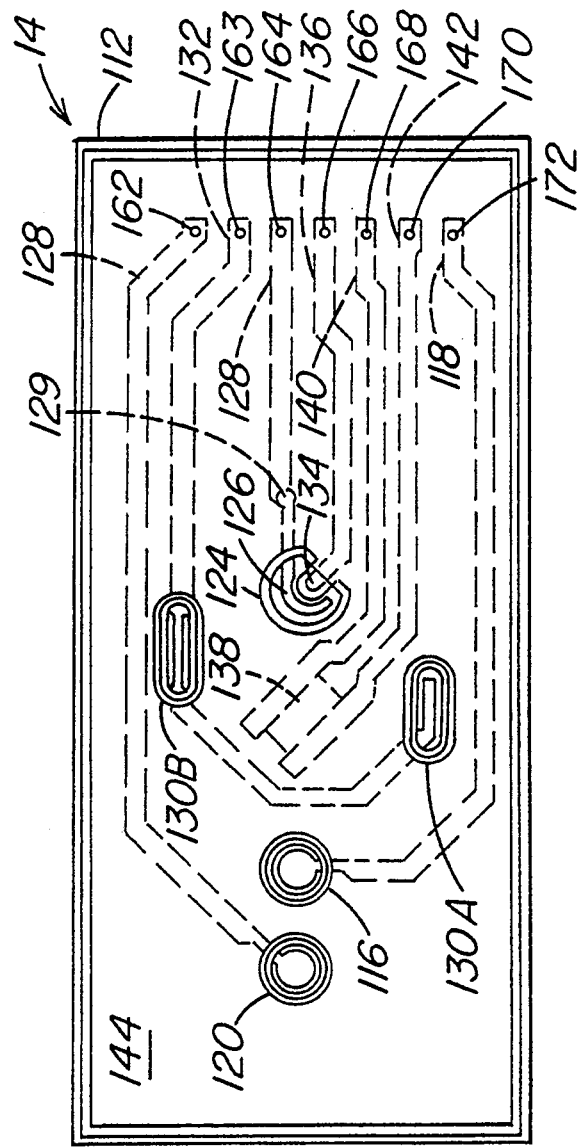
FIG. 21 is a planar view of the one side of the wiring substrate of the present invention, having an arrangement of three analyte sensors with two reference electrodes and a thermistor with accompanying patterned and layered circuitry.

A nonexclusive example of the sensor element is shown in FIGS. 19–22 with the preferred sensor element 14 shown in FIG. 21. The following description of these figures new reference numbers are used for components that may have been previously discussed in regards to the aforedescribed electrochemical sensor assembly.

As previously described the preferred electrical circuitry 20 for the sensor element 14 has several electronic components. This preferred embodiment in shown in FIG. 21. An alternative embodiment utilizing one reference electrode is shown in FIG. 19, which is a top planar view of one side of the wiring substrate, hereinafter referred to as "board" with at least one electrochemical sensor 18 of the present invention, where the components have particular shapes. Any other shapes than those shown in FIG. 19, that are known to those skilled in the art for the particular components, can be used.

The substrate 111 on both sides of the board 14 is any glass or ceramic including sheet or chip or nonconducting substrate like wood or nonconducting polymers or commercially available frit that can be used as the substantially smooth flat surface of the substrate layer 111. Nonexclusive examples include borosilicate glass as is known to those skilled in the art for producing thick film or layered circuits. A nonexclusive but preferred example of which includes a ceramic base having around 96% A1203 such as that available commercially from Coors Ceramic Company, Grand Junction, Colo.

The substrate layer 111 is essentially flat and any substrate known to those skilled in the art for forming printed wiring circuits can be used. It is preferred that the composition of the substrate can endure the presence of electrolyte that has a pH in or over the range of 6 to 9 and remain unaffected for a substantial period of time.

As can best be seen in FIG. 19, the board 14 is provided with a number of electrodes and more particularly, electrodes useful in the measurement of blood gas oxygen, carbon dioxide and pH. The board 14 is also provided with a thermistor and resistor arrangement to indicate the temperature at any time on the board 14 as well as reference electrodes for establishing an accurate reference potential; all of which will be described in further detail below.

On the substrate layer 111 is a patterned metallic layer 113 with a number of extensions which act as the electronic conducting pathway between a voltage or current source external to the board 14 (not shown) and each of the components. The extensions constitute the transmission section, where each extension has a component at its end. The several extensions also have the ability to transmit changes in voltage from the components of the board 14 to the Analyzer (not shown in this Figure).

The pH sensing electrode 115 is located at the end of extension 117; the carbon dioxide sensing electrode 119 is located at the end of extension 122; the oxygen sensor 124 is provided with an anode 126 located at the end of extension 128; the reference electrode 130 is located at the end of extension 132 which extends from anode 126 of the oxygen sensor 124; the oxygen sensor 124 is further provided with a cathode 134 which is located at the end of extension 136; thermistor 138 is located at the end of extensions 140 and 142.

As shown in FIG. 20, the patterned metallic layer 113 has metallic external leads 146–160 on the other side of the substrate 111. Although the external leads are shown on the opposite side of the substrate 111, they can also be on the same surface as their associated metallic lead patterns and components.

External leads 148–158 are conductively associated with the components on the FIG. 19 side of the substrate layer 111 and external leads 146 and 160 are in metallic electrical conducting contact with a thick film heater 174 which is provided on the FIG. 20 side of the substrate layer 111. The heater 174 traverses the board in a serpentine fashion to provide a grid of heat to the nonelectrically conducting substrate and its function will be described below.

External leads 152 and 156 are in metallic electrical conducting contact with a resistor 176 which is also provided on the FIG. 20 side of the substrate layer 111. The resistor is in a half-bridge relationship with the thermistor 138 and, as such, it commonly shares external lead 152 with the thermistor 138; thermistor 138 also being in metallic electrical conducting contact with external lead 152. The function of the thermistor 138 and resistor 176 arrangement will be described below.

The patterned metallic layer 113 is formed by printing pastes deposited onto a substrate in the desired pattern to act as ohmic conductors. Nonexclusive examples of suitable heat resisting metals include; noble metals such as platinum (Pt), ruthenium (Ru), palladium (Pd), rhodium (Rh), iridium (Ir), gold (Au) or silver (Ag) or other metals traditionally used as Clark cells and other ISE's and mixtures thereof. A nonexclusive but preferred example of a suitable paste is a silver paste of the type produced and available from Electro-Science Laboratories, Inc. under the trade designation ESL 99112.

The metallic layer 113 is dried to produce the above noted patterned conductive pathways 117, 122, 128, 132, 136, 138 and 140 of FIG. 19 Any method known to those skilled in the art for producing a sufficient thickness of metallic tracing can be used. Preferably pathway 128 has ground 129.

Preferably, the silver pastes are oven dried and fired at a high temperature in a furnace. Firing can be accomplished at a temperature in the range of around 800° C. to 950° C. for a period of around 1 to 20 minutes. With this procedure, the thickness of the layer of the metallic conducting tracing is usually in the range of around 0.0005 to 0.001 inches. Although the aforementioned are preferred conditions, general conditions for obtaining a proper thickness can be used where the thickness can be generally range from about 0.0004 to 0.0015 inches.

The aforementioned conductive patterns are encapsulated with a glass ceramic mixture or a ceramic insulating material such as alumina or spinal. This encapsulation can range from a total encapsulation to encapsulation except at the end of the metallic pattern.

The aforementioned electrodes are preferably produced by one of the layered circuit techniques. This involves leaving the respective shaped ends uncovered while the metallic patterns are completely covered by the encapsulant. The encapsulation of the metallic patterns can range from encapsulating each from the other to a sufficient degree for electrical insulation of the conductive patterns and any conductive layers from each other.

As shown in FIG. 19, the encapsulant can extend across the whole board from edge to edge as generally shown at numeral 144. Preferably, the thickness of the encapsulant layer is that which is adequate to seal the underlining metallic layer and to provide insulation for the metallic patterns. Preferably, the thickness of the layer is around 120–130 microns.

A preferred glass ceramic mixture useful as the encapsulant is the type produced and available from Electro-Science Laboratories, Inc. under the trade designation ESL 4904.

The several electrodes may be masked during the encapsulation to keep them suitably uncovered for the addition of active materials (e.g. polymer liquids and pre-cut dry film membranes) over the appropriate electrodes on the surface of the substrate layer 111.

This process involves masking the electrodes by the use of polymer film coating on the screen used to screen print the encapsulant. This leaves the underlying silver exposed to form the electrodes for active materials. It is also possible to use multiple layers of the metallic conductive layer or encapsulant.

Preferably, the glass composition for the encapsulant as with the substrate 111 is selected to possess good chemical stability and/or moisture resistance and to possess high electrical insulation resistance. Also, the metallic and encapsulant materials are selected so that they can endure the presence of an electrolyte in a similar manner as the substrate composition.

The geometry of the several electrodes could be made by a laser beam to carve or cut or trim the electrode, however, they are preferably prepared by the aforementioned layered circuit technique.

The serpentine formed heater 174 and the resistor 176 on the FIG. 20 side of the board may be prepared by a number of commercially available techniques, however, they are preferably thick film devices prepared by the aforementioned layered circuit technique.

Holes 162–172 may be drilled by a laser through the substrate 111 to conductively connect the metallic extensions 117, 122, 128, 138, 140 and 136 traced on the FIG. 1 side of the substrate layer 111 with their respective metallic external leads 148–158 on the FIG. 20 side of the substrate layer 111. In general, these openings 162–172 are produced by the focused laser beam drilling a hole by heating a small volume of material to a sufficiently high temperature for localized melting and/or vaporization.

The external leads 146–160 may be produced on the other side of the side of the substrate layer 111 with the see paste and firing as that done for aforementioned metallic patterns. The metallic external leads 146–160 are in metallic electrical conducting contact with the various components on each side of the board. As before mentioned external leads 146 and 160 are in metallic electrical conducting contact with the heater 174 and external leads 152 and 156 are in metallic electrical conducting contact with a resistor 176 which commonly shares external lead 150 with the thermistor 138; thermistor 138 also being in metallic electrical conducting contact with external lead 150. External lead 158 is in metallic electrical conducting contact with the $CO_2$ sensing electrode 119; external lead 148 is in metallic electrical conducting contact with the pH sensing electrode 115; external lead 148 is in metallic electrical conducting contact with the $CO_2$ sensing electrode 119; external lead 152 is in metallic electrical conducting contact with the anode 126 of the oxygen sensor 124, the anode 126 having an electrical ground 129; external lead 152 is also in metallic electrical conducting contact with the reference electrode 130 which is located at the end of extension 132 which extends from anode 126 of the oxygen sensor 124, the anode 126 and external lead 154 is in metallic electrical conducting contact with the cathode 134 of the oxygen sensor 124; external lead 154 is in metallic electrical conducting contact with the cathode 134 of the oxygen sensor 124.

The holes 162–172 have been drilled through the substrate layer 111 and when the metallic layers are screened such electrical connections are formed. Alternatively, the metallic external leads 146–160 can be produced and preferably are produced by a very high powered carbon dioxide laser. This can be accomplished by the supplier of the nonconducting substrate and in this case the metallic layer is added to the substrate so each conducting pathway electrically connects with an external lead.

As described above, the process of masking the electrodes by the use of polymer film coating on the screen, is used to screen print the encapsulant. This leaves the underlying silver exposed to form the electrodes for active materials. It is also possible to use multiple layers of the metallic conductive layer or encapsulant and the outer layer of the encapsulant may be solvent or thermoplastically bondable and may include polymers, as for example, acrylates or polyvinyl chloride as the major component in the encapsulant. The purpose of the outer coating or encapsulant is to enhance bonding of the active materials and, in particular, to provide a reliable surface for the attachment of the liquid or solid film type membrane materials.

Each of the sensing electrodes are fabricated to perform their specific task and may be selected from many commercially available electrode components. The pH electrode 115, $CO_2$ electrode 119 and the Oxygen sensor 124 are each fabricated with a membrane which maintains their respective electrolytes in a fluid tight manner in the cavities or openings in which the electrodes are positioned.

The pH electrode 115 and the $CO_2$ electrode 119 may be similar in regards to the circuit geometry and electrolyte and may be provided with membranes suitable for the particular characteristic being measured.

For pH electrode 115, for example, the use of cation permeable and particularly hydrogen ion permeable membrane may be used. A number of such cationic exchange materials may be utilized, as for example, membranes fabricated from copolymeric vinyl ethers as manufactured by E.I. duPont under registered trademark NAFION.

The membrane for the $CO_2$ electrode 119 may be fabricated from a wide range of commercially available carbon dioxide permeable polymeric materials. The electrolytes of the pH electrode 115 and the $CO_2$ electrode 119 are bound by their respective membranes.

The membrane for the oxygen sensor may be fabricated from a polymeric material such as polystyrene in an organic or inorganic solvent. The oxygen permeable electrolyte of the oxygen sensor 124 bathes the anode 126 and cathode 134 to provide electrical ionic contact between the two. The electrolyte can be any electrolyte known to those skilled in the art for Clark Cell as, for example, a saline solution based on potassium chloride or sodium chloride.

The anode 126 of the oxygen sensor 124 is electrically grounded at 129 to assure that the electrolyte potential does not change and that the opening to the electrolyte is held at some voltage which is the same as the anode potential so that the electrolyte is grounded in the electrode configuration.

The reference electrode 130, which is located at the end of extension 132 and which extends from anode 126 of the oxygen sensor 124, provides a highly stable reference potential. This reference potential provided by the reference electrode 130 facilitates accurate measurement of the blood gases. The reference electrode 130 may be fabricated from a number of suitable materials known to those skilled in the reference electrode art such as a silver and silver chloride composite using the aforementioned layered circuit technique.

The thermistor 138 is a thick film thermally sensitive resistor whose conductivity varies with the changes in temperature. The thermistor 138 may be fabricated from a number semi-conductive materials as, for example, oxides of metals. The thermistor and may be formed and applied to the substrate layer 111 by the use of the aforementioned layered technique. The temperature coefficient of the thermistor 138 is large and negative and is used to sense the temperature of the board 14 at all times when the board 14 is coupled to its associated electronic Analyzer (not shown). It is operated at relatively low current levels so the resistance is affected only by the ambient temperature and not by the applied current.

As before described, external leads 152 and 156 are in metallic electrical conducting contact with a thick film resistor 176 which is provided on the FIG. 20 side of the substrate layer 111. The resistor 76 is in an half-bridge relationship with the thermistor 138 and, as such, it commonly shares external lead 152 with the thermistor 138; thermistor 138 also being in metallic electrical conducting contact with external lead 152. The half-bridge circuit configuration is a voltage divider and generates a ratiometric output to the Analyzer. This is important for it allows the actual resistance values to float and results in highly consistent and accurate temperature sensing and control of the board 14 on a board to board basis. Accuracy and consistency of the resistor 176 and thermistor 138 arrangement is achieved by calibrating the board 14 by laser trimming of the resister 176 to produce zero volts at 37° C. The laser beam is precisely deflected across the thick film resistor 176 to produce the desired temperature voltage relationship. A current is applied at external leads 150 and 152 by the Analyzer until zero volts is achieved. This gives a linear output so that the temperatures can be measured other than 37° C. from the slope of the line from the calibration at room temperature and 37° C. The resister 176 has essentially zero temperature coefficient and, accordingly, may be placed without any adverse effect on the sensing capability of the associated thermistor 138, on the FIG. 20 side of the board 14 with the heater 174.

Accurate sensing of the ambient temperature of the board 14 is required to precisely control the heater 174 to ultimately maintain, within a narrow distribution of temperatures, the desired operating surface temperature on the FIG. 19 or sensor side of the board 14.

Placement of the thermistor 138 can affect the accuracy of the measurement of the temperature. As can be seen in FIG. 19, the thermistor 138 is placed in the same plane and in close relation to the sensors 115, 119 and 124 to thereby accurately sense the ambient temperature at or near such sensors. This physical placement of the thermistor 138 allows for the rapid adjustment of the heater 174 by the Analyzer to maintain the desired operating temperature. The thermistor 138 resistor 176 arrangement provides for very accurate temperature measurement. This physical placement of the thermistor 138, so close to the sensors, requires that it be correctly fabricated to ensure that it is electrically isolated from the electrolytes of the several sensors. The encapsulant for the thermistor 138 must be thick enough to accomplish the electrical isolation yet thin enough so as not to lose any response time.

The heater 174, provided on the FIG. 20 side of the board 14, rapidly and accurately produces the necessary heat in response to any temperature change sensed by the thermistor 138; the thermistor 138 and the several sensors 115, 119, and 124 all being in the heated region produced by the heater 174. Thick film heaters are not generally considered to be rapid response devices and their heat output tends to take a relatively long time, in terms of electronic devices, to change. To improve the responsiveness of the heater 174, it is powered by a controlled DC voltage whereby the heater is regulated by a combination of proportional (P), integral (I) and/or derivative (D) controls, preferably PID control thereby reducing the amount of overshooting or undershooting by the heater of a predetermined temperature. This not only increases the responsiveness of the heater 174 but also allows for better overall thermal control including avoiding the heater 174 from overshooting or undershooting the desired temperature.

The timing sequence for the production of the heat by the heater 174 to the several sensors is provided by the natural state of power supplied to the board 14 when it is connected to the Analyzer. This same power will also produce the read-out from the measurements by the sensors of the blood gas oxygen, carbon dioxide and pH. This timing sequence facilitates a room temperature calibration of the board 14; an elevated temperature calibration at 37° C. and then the measurement of the blood gas oxygen, carbon dioxide and pH.

Prior to any measuring of the blood gases by the several sensors 115, 119 and 124, all or part of the board 14 may be exposed to or stored with a calibration liquid, with the several sensors being exposed to the fluid. To measure the blood gases, the several sensors are brought in contact with the volume of the blood sample to be measured. The volume of the blood sample may be quite small, ranging from as small as a few microliters.

FIGS. 21 shows the preferred embodiment of the substrate of the present invention where two reference electrodes 130A and 130B are present in offline alignment to the alignment of the sensors 119, 115 and 124 and thermistor 138. The axial alignment shown in FIG. 21 allows the sensors to be in contact with a sample in a chamber covering their alignment, while the reference electrodes can be in contact with reference fluid or electrolyte in another chamber placed in fluid contact with the reference electrodes. Any alignment pattern can be used that separates the reference electrode from the sensors in the aforedescribed manner. The other components of the wiring board are as described for the other figures.

Figure 22:
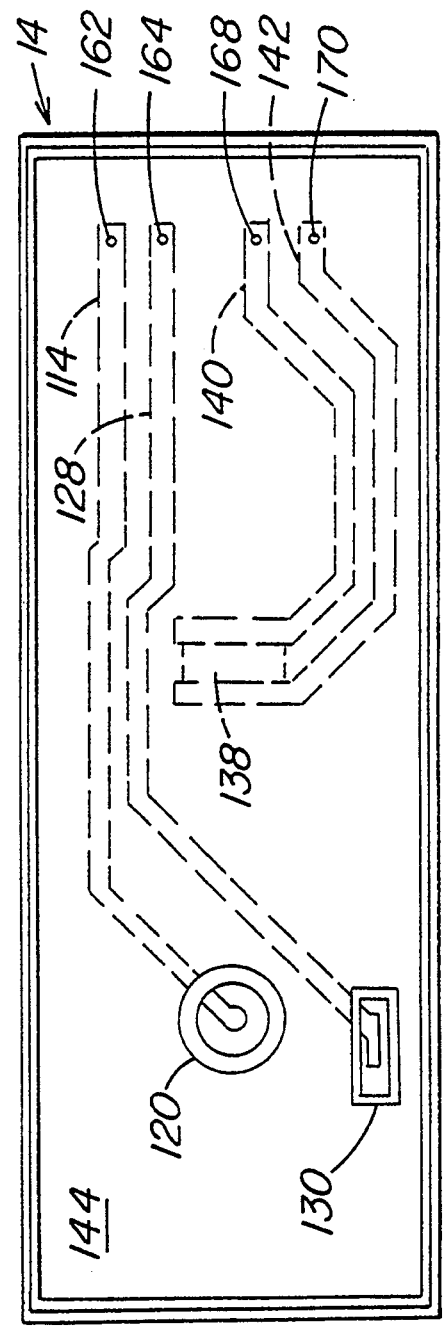
FIG. 22 is a planar view of the one side of the wiring substrate of a broad aspect of the present invention having one sensor and a thermistor axially aligned and one reference electrode spaced apart from that axis and having accompanying patterned and layered circuitry.

FIG. 22 shows a broader aspect of the invention where only one sensor 119 is present with one reference electrode 130. If the sensor does not require a reference electrode as in the case of most amperometric electrodes the reference electrode need not be present.

Figure 23:
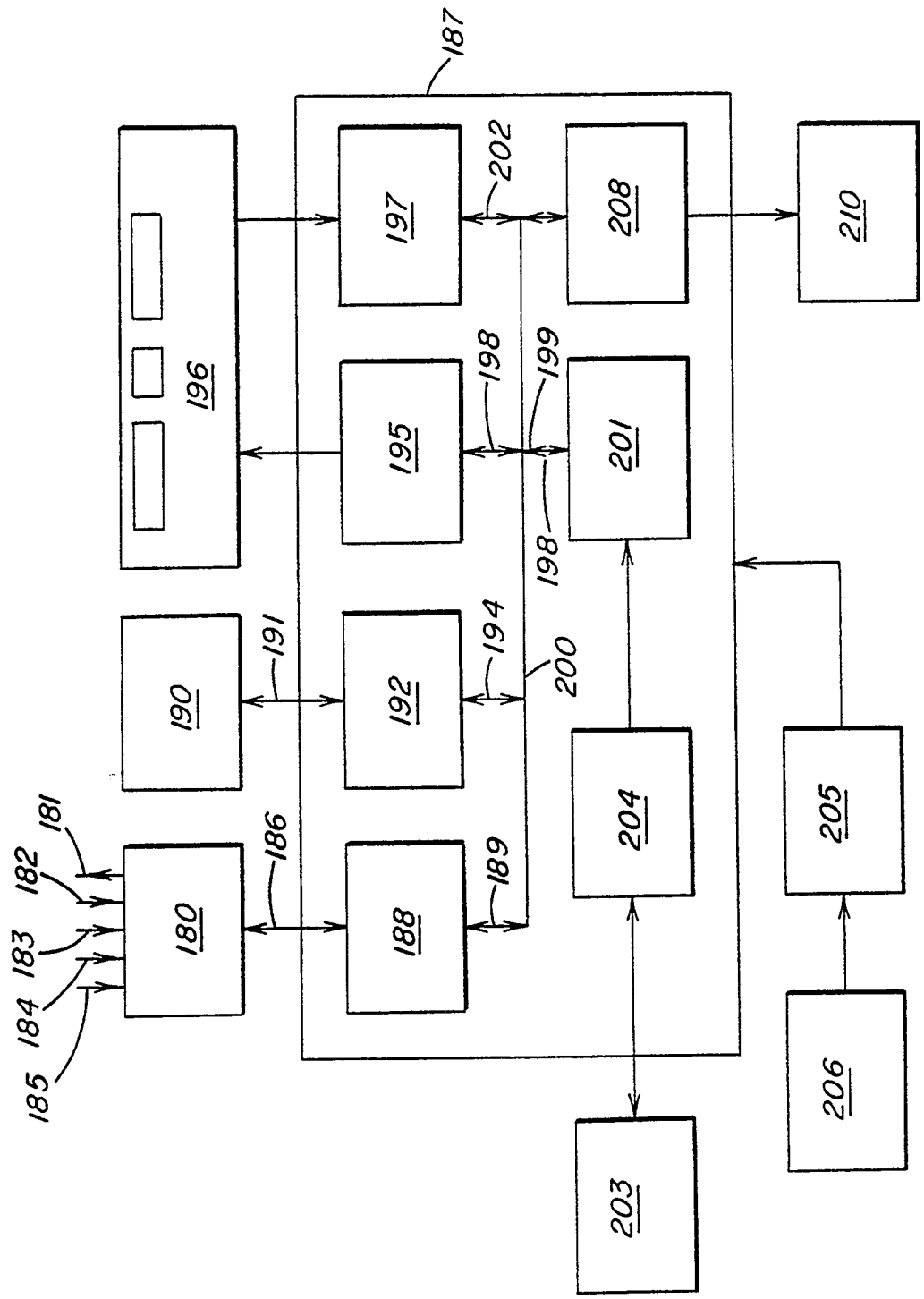
FIG. 23 is a block diagram of the monitoring means and its connection with the electronic wiring substrate.

FIG. 23 shows the block diagram of the functions and interrelationship of these functions for the Analyzer with its electrical connection to the sensor element 14 of FIGS. 1–22. The analog input processing unit 180 of the Analyzer 12 interfaces with the electric circuitry 20 of the previous figures by the electrical connector 16 to allow signals from the sensors 18 and any temperature detector 138 of FIGS. 19–22. Also the electrical connection 16 allows for electrical current to be supplied to any heater 174 and resistor 176 on board 14 as shown in FIG. 20 and for any current or voltage that may be needed by the sensors 18 on the board 14. The electrical connections can be separate but are preferably individual connections in a bundle connector or ribbon cable.

Connection 181 can carry current to an amperometric oxygen sensor 124 of FIG. 19. Respectively, connections 182, 183, 184, and 185 can carry signal and/or supply current or voltage to: the sensors 115 and 119, the thermistor 138, and heater 174 all shown in the previous FIGS. 19 and 20. The processing unit 180 can be electrically connected to the microcomputer 187 by 186 to the function of a 12 bit analog to digital converter 188. Converter 188 can be electrically connected by 189 to line 200 a type of buss line. Through line 200 connections are made to the central processing unit (CPU) 201 which has is a date/time circuit and battery backup random access memory device and can be and preferably is an 8-bit central processing unit (CPU) microprocessor. In addition the encoded information reader and drive circuit unit 190 is connected by line 191 to the microprocomputer 187 through Input/Output (I/O) port 192 for two way communication. The CPU is connected through I/O port 195 to the display and keyboard unit 196, and this unit is connected through I/O port 197 and through line 202 to line 200 for communication with the microcomputer 187. The CPU 201 is connected for external communication by RS232 and drive circuit unit 203 through serial port 204. The microcomputer 187 is connected to a power supply 205 and battery pack 206 for power. Also input output port 208 is connected electrically to a printer mechanism 210 for a hard copy display.

In the preferred embodiment, the printed wiring board whose functions are depicted in FIG. 23 is divided into two boards subassemblies. First a primary board subassembly which is divided into five subsystems: the microcomputer, the bar code reader system, the printer subsystem, the sensor input circuits, and the RS232 drive circuit. The second subassembly is the power supply board subassembly which is a switch power supply with four outputs. One pair provides ±5 volts for the digital and the analog circuits. The other pair provides an isolated ±5 volts for the RS232 drive circuits. The microcomputer consists of four major subsections—the central processing unit, the program memory, the random axis memory, and address decoder and the analog digital converter. The CPU is preferably an 80 C51FA8 bit CMOS microcontroller with a 256×8 internal random axis memory and four 8 bit bi-directional parallel ports and three 16-bit timer/event counters and with full duplex programmable serial interface and reduced power modes. The CPU can address 64,000 bits of programmed memory and 64,000 bits of random access memory or memory map input/output. The program memory is preferably a 27G256 which is a high-density CMOS electrically programmable read only memory organized as a 32,768×8 configuration. The random access memory is divided into two types. First an 8,000×8 volatile static random access memory and a 2,000×8 nonvolatile RAM with a built-in real time clock that uses an embedded lithium energy cell to maintain the watch information and retain the RAM data for over five years. The address decoder is a GAL that selects seven memory mapped areas of random access memory and two are selected as data memory and the rest are selected as inputs or outputs. The analog digital converter is an ML2208 data acquisition peripheral that has an eight channel single ended multiplexer, a programmable game instrumentation amplifier, a 2.5 volt band gap reference, and a 12-bit+analog to digital converter with built-in sample-and-hold. The 8D converter interfaces to the microcontroller through the general purpose 8-bit port. Also, the ML2208 includes a programmable processor, data buffering, a 16-bit timer and limit alarms. The bar code read system consists of a 70 nanometer precision optical reflective sensor and the system uses the HPHBCS-1100 sensor and HP sapphire lens. A printer subassembly is a thermal printer subassembly having four main components—the 8-bit latch, a printer head drive, a motor drive circuit and the printer mechanism. The sensor input circuits are analog signal conditioning circuits that receive the signals from the sensors and electronically control the sensors. There are two types of signals from the sensors, voltage or current. In addition, there is the heater control circuit. The serial or port driver circuit consists of the RS232 input buffer and line driver that are optically isolated from the internal circuits of the analyzer. Isolation is necessary in order to comply with the UL544 leakage current requirement. The power supply circuit supplies the five volts to the logic circuits and the analog circuit and an isolated five volts for the serial port. Power to the printer motor and printer heads is supplied directed from the battery pack which is typically six volts.

Any components known to those skilled in the art to accomplish the aforementioned functions can be used in the analyzer and the electrical circuitry of the present invention.

Although a particular preferred arrangement for the functional units of the Analyzer has been specifically set forth variations are possible that may delete one or more of the functional units. As long as the processing unit 180, and converter unit 188 are present when analog signals are used, and a processor is functionally tied into these units and power is supplied and a read out can be obtained the Analyzer is usable for use with the sensor element 14 in the housing of previous figures. Appropriate software resides in the CPU to accomplish these connections and to convert signals from the sensors and to perform the calibration and analysis of samples and to give values indicating the specific amounts of the known types of analytes present in the analyzed fluids.

We claim:

1. An apparatus having a preconditioned sensor and electronic circuit, comprising:

nonconducting substrate with at least one electrochemical sensor and with electrical circuitry in electrical contact with the sensor to convey electrical impulses from the sensor, housing having at least one part enclosing the nonconducting substrate and forming a channel in fluid contact with the at least one sensor on the substrate, wherein the channel has two openings form the housing for fluid flow through the channel and that is in fluid contact with the at least one sensor on the substrate to allow fluid in the channel to be in fluid contact with the sensor where one opening is adapted for receipt of a fluid sample for measurement of a component by the sensor, and another opening is positioned in the channel after the at least one sensor, fluid occupying a substantial portion of the channel to precondition the membrane of the one or more sensors, seals that are substantially impervious to at least moisture associated with the channel to maintain the hydrating fluid in contact with one or more sensors and to minimize the transport of hydrating fluid away from contact with the one or more sensors, electrical attachment means electrically associated with the circuit means of the substrate to convey the sensor signals from the apparatus for interpretation, wherein the hydrating fluid is electrically isolated from the electric circuitry of the substrate and the electrical attachment means.

2. Apparatus of claim 1 wherein the at least one electrochemical sensor on the substrate is an analyte sensor to detect one or more analytes in fluid.

3. Apparatus of claim 2 wherein the at least one electrochemical sensor is a gas sensor to measure blood gas analytes in blood.

4. Apparatus of claim 1 wherein the substrate is ceramic and has three sensors, one for measuring the partial pressure of oxygen, another for measuring the partial pressure of carbon dioxide and another of measuring the pH of a fluid like blood.

5. Apparatus of claim 1 wherein substrate has the electrical circuitry designed to enhance electrical isolation from the hydrating fluid.

6. Apparatus of claim 1 wherein housing has at least two sections and both sections have at least one set of attachment means for suitable attachment of the two sections to enclose the substrate in the internal space.

7. Apparatus of claim 6 wherein the housing has a channel formed by one section of the housing and the substrate within the internal space between the sections of the housing.

8. Apparatus of claim 7 wherein the housing has the channel extending along a longitudinal axis in a near linear orientation from one end of the housing to the other.

9. Apparatus of claim 8 wherein the housing has the channel emerging from each end of the housing in tips for attachment to a sample collection device at one end and a sample disposal device at the other end.

10. Apparatus of claim 8 wherein the housing includes one or more adhesive ports filled with cured adhesive.

11. Apparatus of claim 1 wherein the housing has one or more side channels fluidly connected to the channel that has openings from the housing that where the side channels have fluid selected from the group consisting of preconditioning fluid and hydrating fluid and mixtures thereof.

12. Apparatus of claim 11, wherein the housing and the substrate are associated with each other so that the side channels have one or more reference electrodes that are present on the substrate.

13. Apparatus of claim 12, wherein the polymers are selected from the group consisting of: methyl methacrylate styrene butadiene terpolymer, polyesters and polycarbonate.

14. Apparatus of claim 1 wherein the housing has a slot for the ingress and egress of the electronic attachment means.

15. Apparatus of claim 1 wherein the preconditioning fluid is a hydrating fluid that is isotonic with the hydrated state of the submembrane of the sensor.

16. Apparatus of claim 1 wherein the seals are located one at each opening of the channel from the housing.

17. Apparatus of claim 1 wherein the seals are substantially impervious to oxygen and carbon dioxide.

18. Apparatus of claim 1 wherein the seals have inner surface attached to the housing covering the opening of the channel and outer surface, where the outer surface is metal and the inner surface is an adhesive type polymer, where said seal covers the opening of the channel by the inner adhesive surface being stuck to at least a portion of the housing surrounding opening of the channel.

19. Apparatus of claim 18, wherein seals are multilayer seals with the exterior surface is a metal foil and the interior surface is a polymeric layer selected from the group consisting of: polyethylene, polypropylene, polyvinylidene chloride and nylon and where the thickness of the seals is in the range from around 1 to around 10 mils.

20. Apparatus of claim 19, wherein the multilayer seals are a three layer laminate having an exterior surface selected from the group consisting of nylon, polyester, polyethylene and polypropylene, and an intermediate layer of aluminum foil and an inner heat sealable polymeric layer selected from the group consisting of: polyethylene, polypropylene, polyvinylidene chloride and nylon.

21. Apparatus of claim 1 wherein the seals are induction sealed to the housing over the channel openings.

22. Apparatus of claim 1 wherein the seals are heat sealed to the housing over the channel openings.

23. Apparatus of claim 1 wherein the seals are flexible generally circular disc having a generally circular periphery and a diameter such as to circumferentially seal the openings of the channel.

24. Apparatus of claim 1, which includes an electrically isolating means to isolate the electric circuit means on the substrate and the hydrating fluid, where the electrically isolating means occupies the internal space not already occupied by other components, and wherein the electrically isolating means is placed in the housing through a hole in the housing.

25. Apparatus of claim 1 wherein the apparatus is gamma-sterilized.

26. Apparatus of claim 1 wherein the nonconducting substrate with at least one preconditioned electrochemical sensor and with electrical circuitry in electrical contact with the sensor is comprised of: the nonconducting substrate, thermistor and at least one analyte sensor supported, in close relation, one to the other, on the substrate and a heater, also supported on the substrate, to provide heat in response to temperature sensed by said thermistor to at least the region where said thermistor and said blood gas sensor are positioned on said board to thereby control the temperature of said region of said board within a said board for connecting said board to an external electrical source.

27. Apparatus of claim 26 wherein said board is manufactured using thick film layered circuit technique.

28. Apparatus of claim 26 wherein said thermistor and said blood gas sensors are supported in the same plane on said board.

29. Apparatus of claim 26 wherein said blood gas sensors includes at least an oxygen sensor.

30. Apparatus of claim 26 wherein said blood gas sensors includes at least a carbon dioxide sensor.

31. Apparatus of claim 26 wherein said blood gas sensors includes at least a pH sensor.

32. Apparatus of claim 26 wherein said blood gas sensors include an oxygen sensor, a carbon dioxide sensor and a pH sensor.

33. Apparatus of claim 26 wherein said connecting means includes plurality of external leads, a resistor is supported on said board on the same side as said heater and commonly connected to one of said external leads with said thermistor, dividing the voltage therebetween.

34. Apparatus of claim 26 wherein the temperature coefficient of said thermistor is negative or positive and the temperature coefficient of said resistor is around zero, and where the divided voltage is proportional or inversely proportional to temperature, the this output is used to measure temperature.

35. Apparatus of claim 26 wherein said connecting means further includes a plurality electronic conducting pathways individually and electrically connecting each of said sensors and said thermistor with external leads provided on said board at the end of said pathways.

36. Apparatus of claim 26 wherein said resistor and said heater are each electrically connected to external leads.

37. Apparatus of claim 26 wherein said heater is powered by pulsed DC whereby said heater is continually turned on and off thereby avoiding said heater from overshooting or undershooting a predetermined temperature.

38. Apparatus of claim 26 wherein said external leads are positioned on the same side of said board as said resistor and said heater.

39. Apparatus of claim 26 wherein said electronic conducting pathways individually and electrically connecting each of said sensors and said thermistor on one side of said board with external leads provided on the other side of said board through a plurality of holes in said board.

40. Apparatus of claim 26 wherein said resistor is a laser trimmed resistor.

41. Apparatus of claim 26 wherein said oxygen sensor is an electrochemical cell and includes a anode and a cathode, each connected to an external lead.

42. Apparatus of claim 26 wherein said oxygen sensor includes an oxygen permeable membrane covering, in a fluid tight manner, an opening in said board containing an electrolyte, said anode being grounded on said board to thereby assure that potential of said electrolyte is the same as the anode potential.

43. Apparatus of claim 26 wherein there is at least one reference electrode, to provide an accurate reference potential, supported on said board and is electrically connected to a electronic conducting pathway.

44. Apparatus of claim 26 wherein there is one reference electrode supported on said board and is electrically connected to a electronic conducting pathway extending from said anode.

45. Apparatus of claim 26 wherein said board includes a patterned metallic layer provided on said ceramic substrate layer.

46. Apparatus of claim 26 wherein said metallic layer is a deposited metallic printing paste on said substrate forming electronic conducting pathways and the electrodes of said sensors and the electrode of a reference electrode, and wherein said metallic layer has at least one encapsulating layer of a chemically stable and moisture resistant encapsulant, and wherein said board includes a thermistor provided on ceramic substrate layer, said thermistor is encapsulated with at least one thin layer of a chemically stable and moisture resistant encapsulant.

47. Apparatus of claim 1 wherein the one or more sensors are prepared by the thick film process.

48. Apparatus of claim 47 wherein both the one or more sensors and the electrical circuitry are prepared by the thick film process.

49. Apparatus of claim 1, wherein the housing around the channel is a rigid molded polymer selected from the group consisting of: thermoplastic polymers and thermosetting polymers.

50. A preconditioned electrochemical sensor assembly, comprising:
 1) a housing having a first and second exterior surface mated for attachment to each other to form an interior space that has an opening from the housing and to form a channel that communicates with the interior space and that has two openings from the housing for fluid flow through the channel where at least one opening is adapted for contact with a fluid sample gathering means,
 2) nonconducting substrate with a plurality of hydratable electrochemical sensors and with electrically isolated electrical circuitry means in electrical contact with the sensors to convey electrical impulses from the sensors and adapted for location within the interior space of the housing to communicate with the channel to have the sensors arranged for fluid contact with any fluid in the channel,
 3) hydrating fluid occupying a substantial portion of the channel to hydrate the membrane of the sensor,
 4) seals that are substantially impervious to at least moisture placed in the channel to maintain the hydrating fluid in contact with one or more sensors and to minimize the transport of moisture away from contact with the one or more sensors to hydrate the membrane of the sensor, gas adhering to the housing to cover each opening,
 5) electrical isolating means occupying the interior space of the housing around the nonconducting substrate to isolate the electrical circuitry connected to the sensor from the channel and the hydrating fluid contained in the channel.

51. Apparatus of claim 50 wherein the electrical isolating means is a hardened epoxy polymer.

* * * * *